United States Patent
Yeung et al.

(10) Patent No.: US 10,238,762 B2
(45) Date of Patent: Mar. 26, 2019

(54) INCORPORATING METALS, METAL OXIDES AND COMPOUNDS ON THE INNER AND OUTER SURFACES OF NANOTUBES AND BETWEEN THE WALLS OF THE NANOTUBES AND PREPARATION THEREOF

(71) Applicant: The Hong Kong University of Science and Technology, Hong Kong (CN)

(72) Inventors: King Lun Yeung, Hong Kong (CN); Shammi Akter Ferdousi, Hong Kong (CN); Wei Han, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 1167 days.

(21) Appl. No.: 14/385,852

(22) PCT Filed: Mar. 19, 2013

(86) PCT No.: PCT/CN2013/000320
§ 371 (c)(1),
(2) Date: Sep. 17, 2014

(87) PCT Pub. No.: WO2013/139174
PCT Pub. Date: Sep. 26, 2013

(65) Prior Publication Data
US 2015/0050494 A1     Feb. 19, 2015

Related U.S. Application Data

(60) Provisional application No. 61/685,482, filed on Mar. 19, 2012.

(51) Int. Cl.
B01J 32/00     (2006.01)
A61L 2/238    (2006.01)
(Continued)

(52) U.S. Cl.
CPC .............. A61L 2/238 (2013.01); B01D 15/22 (2013.01); B01J 20/06 (2013.01); B01J 20/3078 (2013.01);
(Continued)

(58) Field of Classification Search
CPC ....... A61L 2/238; B01J 20/3078; B01J 20/06; B01J 37/06; B01J 37/10; B01J 37/346;
(Continued)

(56) References Cited

U.S. PATENT DOCUMENTS

2010/0044630 A1     2/2010   Kang et al.

FOREIGN PATENT DOCUMENTS

| CN | 101302036 A | 11/2008 |
|----|-------------|---------|
| CN | 101607736 A | 12/2009 |

(Continued)

OTHER PUBLICATIONS

Chan, Y, Zhang, X, Zhang, W, Yang, Z and Wang, N 2003, 'Formation mechanism of TiO2 nanotubes', Applied Physics Letters, vol. 82, No. 2, pp. 281-283.*

(Continued)

*Primary Examiner* — Richard M Rump
(74) *Attorney, Agent, or Firm* — Nath, Goldberg & Meyer; Jerald L. Meyer; Stanley N. Protigal

(57) ABSTRACT

A multi-walled titanium-based nanotube array containing metal or non-metal dopants is formed, in which the dopants are in the form of ions, compounds, clusters and particles located on at least one of a surface, inter-wall space and core of the nanotube. The structure can include multiple dopants, in the form of metal or non-metal ions, compounds, clusters or particles. The dopants can be located on one or more of on the surface of the nanotube, the inter-wall space (inter-layer) of the nanotube and the core of the nanotube. The nanotubes may be formed by providing a titanium precursor, (Continued)

converting the titanium precursor into titanium-based layered materials to form titanium-based nanosheets, and transforming the titanium-based nanosheets to multi-walled titanium-based nanotubes.

23 Claims, 24 Drawing Sheets

(51) Int. Cl.
| | |
|---|---|
| *B82Y 30/00* | (2011.01) |
| *B01J 37/06* | (2006.01) |
| *B01J 37/10* | (2006.01) |
| *B01J 37/34* | (2006.01) |
| *B01J 21/06* | (2006.01) |
| *B01J 23/06* | (2006.01) |
| *B01J 23/22* | (2006.01) |
| *B01J 23/42* | (2006.01) |
| *B01J 23/44* | (2006.01) |
| *B01J 23/50* | (2006.01) |
| *B01J 23/52* | (2006.01) |
| *B01J 23/72* | (2006.01) |
| *B01J 23/75* | (2006.01) |
| *B01J 35/00* | (2006.01) |
| *B01J 35/10* | (2006.01) |
| *B01J 37/02* | (2006.01) |
| *C30B 29/60* | (2006.01) |
| *C01G 23/00* | (2006.01) |
| *C01G 23/053* | (2006.01) |
| *C30B 7/10* | (2006.01) |
| *C30B 29/02* | (2006.01) |
| *B01D 15/22* | (2006.01) |
| *B01J 20/06* | (2006.01) |
| *B01J 20/30* | (2006.01) |
| *B82Y 40/00* | (2011.01) |
| *B82Y 99/00* | (2011.01) |

(52) U.S. Cl.
CPC .............. *B01J 21/063* (2013.01); *B01J 23/06* (2013.01); *B01J 23/22* (2013.01); *B01J 23/42* (2013.01); *B01J 23/44* (2013.01); *B01J 23/50* (2013.01); *B01J 23/52* (2013.01); *B01J 23/72* (2013.01); *B01J 23/75* (2013.01); *B01J 35/002* (2013.01); *B01J 35/004* (2013.01); *B01J 35/0013* (2013.01); *B01J 35/1019* (2013.01); *B01J 37/0201* (2013.01); *B01J 37/06* (2013.01); *B01J 37/10* (2013.01); *B01J 37/346* (2013.01); *B82Y 30/00* (2013.01); *C01G 23/005* (2013.01); *C01G 23/053* (2013.01); *C30B 7/10* (2013.01); *C30B 29/02* (2013.01); *C30B 29/602* (2013.01); *B82Y 40/00* (2013.01); *B82Y 99/00* (2013.01); *C01P 2002/82* (2013.01); *C01P 2002/84* (2013.01); *C01P 2002/85* (2013.01); *C01P 2004/04* (2013.01); *C01P 2004/13* (2013.01); *C01P 2004/16* (2013.01); *C01P 2004/20* (2013.01); *C01P 2004/51* (2013.01); *C01P 2004/53* (2013.01); *C01P 2006/12* (2013.01); *Y10S 977/734* (2013.01); *Y10S 977/811* (2013.01); *Y10S 977/845* (2013.01); *Y10S 977/846* (2013.01); *Y10S 977/847* (2013.01); *Y10S 977/902* (2013.01); *Y10T 428/2935* (2015.01)

(58) Field of Classification Search
CPC . B01J 21/063; B01J 23/44; B01J 23/06; B01J 37/0201; B01J 35/1019; B01J 35/004; B01J 35/002; B01J 35/0013; B01J 23/75; B01J 23/72; B01J 23/52; B01J 23/50; B01J 23/42; B01J 23/22; B01D 15/22; C01G 23/005; C01G 23/053; B82Y 30/00; B82Y 99/00; B82Y 40/00; Y10T 428/2935; Y10S 977/845; Y10S 977/846; Y10S 977/811; Y10S 977/902; Y10S 977/847; C01P 2004/16; C01P 2004/13; C01P 2006/12; C01P 2002/85; C01P 2002/84; C01P 2002/82; C01P 2004/53; C01P 2004/51; C01P 2004/20; C01P 2004/04; C30B 29/02; C30B 7/10; C30B 29/602
See application file for complete search history.

(56) References Cited

FOREIGN PATENT DOCUMENTS

| CN | 101766840 A | | 7/2010 |
|---|---|---|---|
| CN | 101786005 A | | 7/2010 |
| CN | 101955223 A | | 1/2011 |
| CN | 102122580 A | * | 7/2011 |
| CN | 102500388 A | | 6/2012 |

OTHER PUBLICATIONS

Kuvarega, Alex T., Rui WM Krause, and Bhekie B. Mamba. "Nitrogen/palladium-codoped TiO2 for efficient visible light photocatalytic dye degradation." The Journal of Physical Chemistry C 115.45 (2011): 22110-22120.*

Yu, Kuo-Pin, et al. "Pt/titania-nanotube: A potential catalyst for CO 2 adsorption and hydrogenation." Applied Catalysis B: Environmental 84.1 (2008): 112-118.*

Ou, Hsin-Hung, Shang-Lien Lo, and Ching-Hui Liao. "N-Doped TiO2 Prepared from Microwave-Assisted Titanate Nanotubes (Na x H2− x Ti3O7): The Effect of Microwave Irradiation during TNT Synthesis on the Visible Light Photoactivity of N-Doped TiO2." The Journal of Physical Chemistry C 115.10 (2011): 4000-4007.*

Cui, L., et al. "Facile microwave-assisted hydrothermal synthesis of TiO 2 nanotubes." Materials Letters 75 (2012): 175-178.*

* cited by examiner

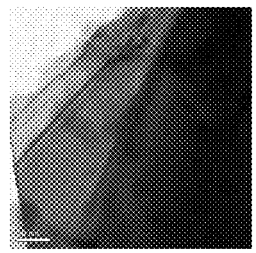
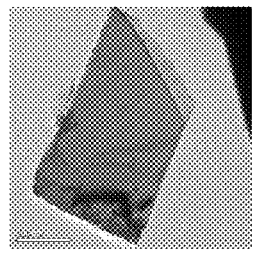
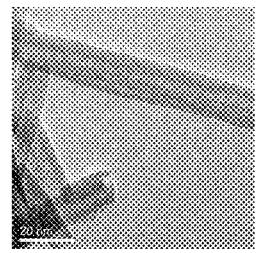
*Fig. 2T*  *Fig. 2U*  *Fig. 2V*
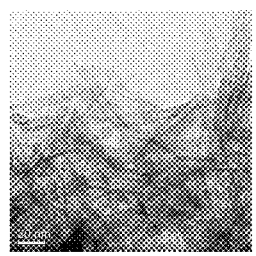
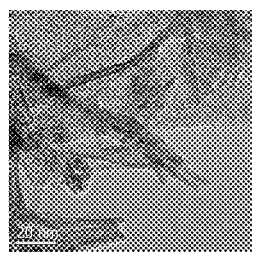
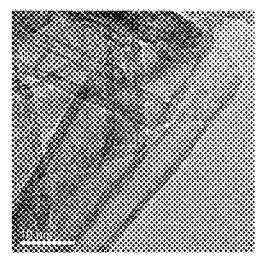
*Fig. 2W*  *Fig. 2X*  *Fig. 2Y*
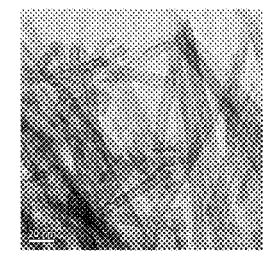
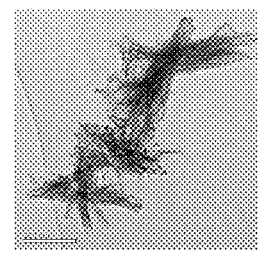
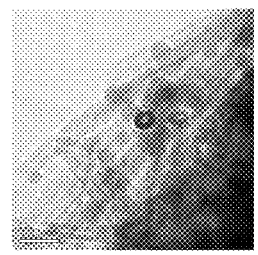
*Fig. 2Z*  *Fig. 2AA*  *Fig. 2AB*

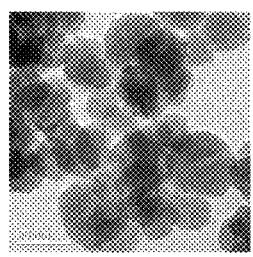 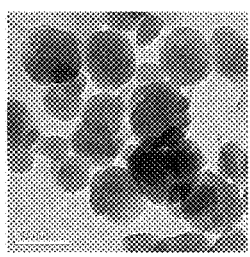 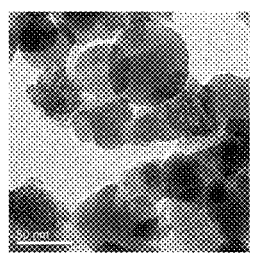 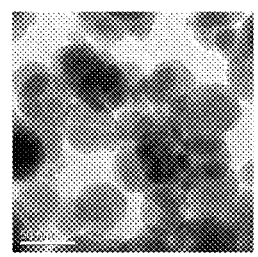
*Fig. 4A*     *Fig. 4B*     *Fig. 4C*     *Fig. 4D*
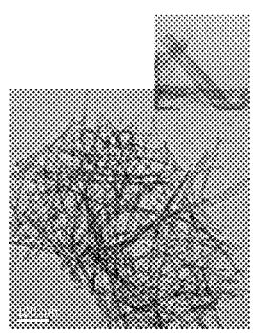  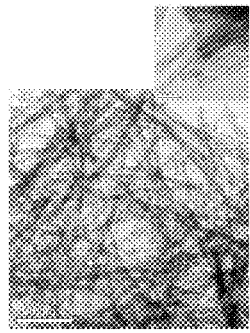 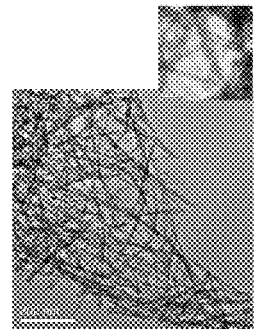
*Fig. 4E*     *Fig. 4F*     *Fig. 4G*     *Fig. 4H*

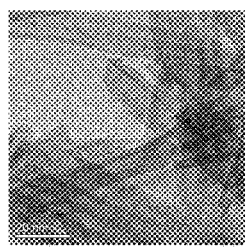 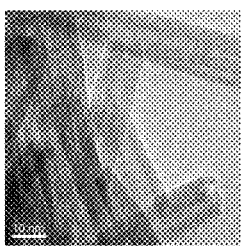 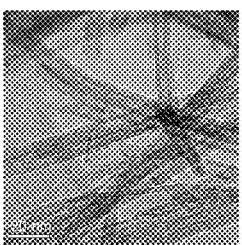 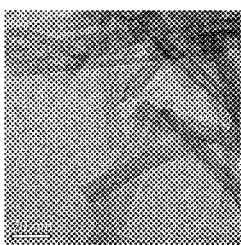
*Fig. 5A*   *Fig. 5B*   *Fig. 5C*   *Fig. 5D*
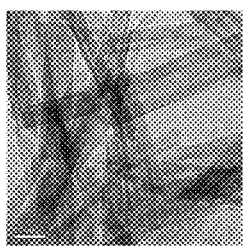 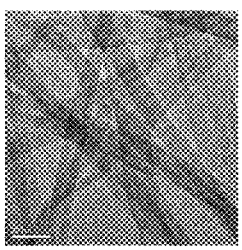 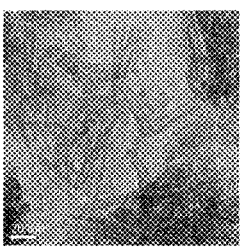 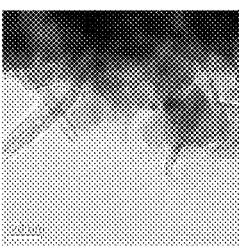
*Fig. 5E*   *Fig. 5F*   *Fig. 5G*   *Fig. 5H*

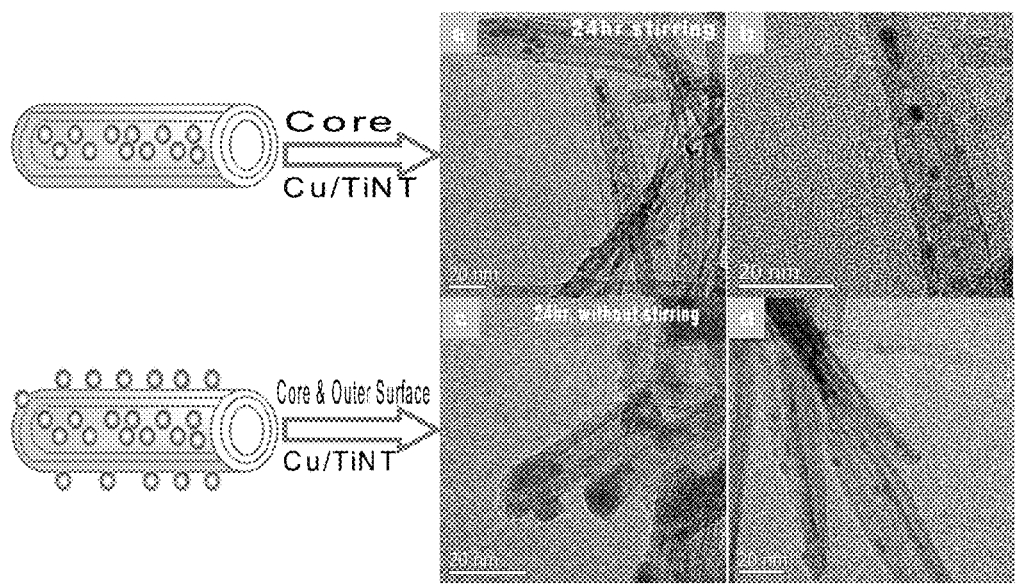
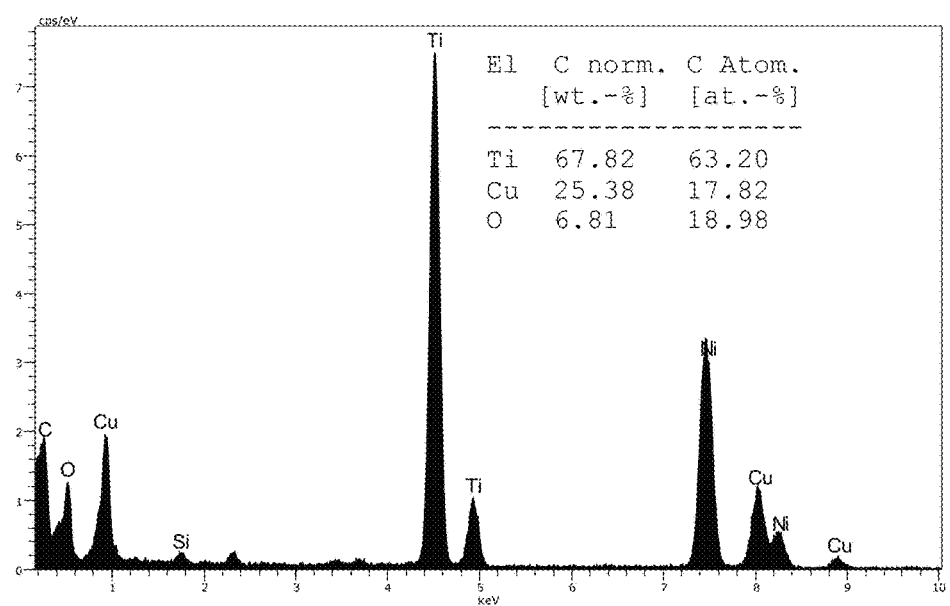
Fig. 26

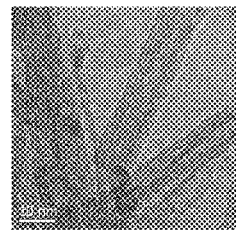 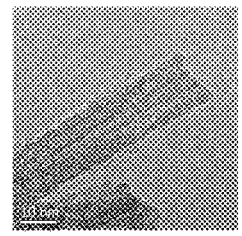 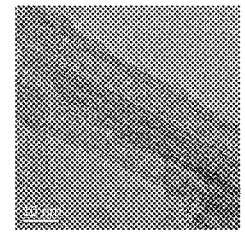
*Fig. 28A*  *Fig. 28B*  *Fig. 28C*
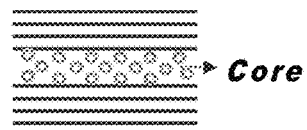
*Fig. 28D*
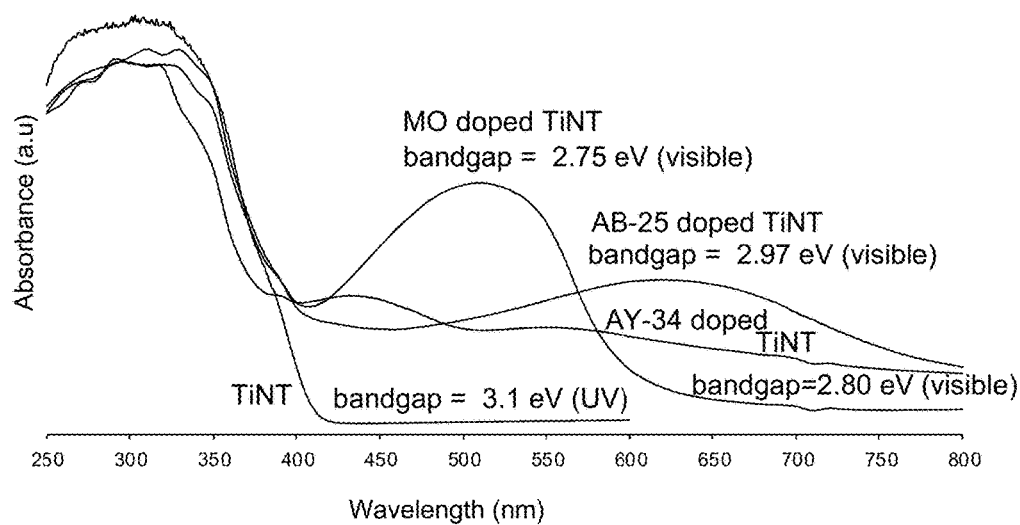
*Fig. 29*

INCORPORATING METALS, METAL OXIDES AND COMPOUNDS ON THE INNER AND OUTER SURFACES OF NANOTUBES AND BETWEEN THE WALLS OF THE NANOTUBES AND PREPARATION THEREOF

RELATED APPLICATION(S)

The present Patent Application claims priority to Provisional Patent Application No. 61/685,482, filed Mar. 19, 2012, which is assigned to the assignee hereof and filed by the inventors hereof and which is incorporated by reference herein.

BACKGROUND

Field

The disclosed technology relates to a manufacturing titanate nanostructure such as nanosheets, nanotube, nanofiber, nanocomposite (0D nanoparticle and 1D nanotube) structures, via in situ and ex situ processes based on titanium precursors.

Background

Titanium nanomaterials comprising a metal or metal oxide with one dimensional nanostructures, or nanomaterials comprising a composite material of an inorganic or organic compound and a metal oxide having nanotube structures have been found to have different physical and chemical properties from the corresponding bulk materials.

Methods for producing titanate nanotubes and other nanostructured materials under hydrothermal conditions have been reported. Published European Application No. 0 832 847 describes this conventional method for producing titanate nanotubes with a diameter 5~50 nm by alkaline treatment of titanium oxide. In this method, titanium dioxide is heated with sodium hydroxide for 1-50 hours at a temperature of 18 to 160° C. The product obtained is washed with water and neutralized. To increase the crystallinity of the product, thermal treatment is done in the range of 300-800° C. for 60 to 160 minutes. At a temperature above 180° C., no nanotubes with required characteristics are obtained.

After this, further studies have been carried out to apply this method to other materials. For example, US Published Patent Application No. 2010/0284902 described this method for producing alkaline sodium titanate nanotubes to obtain or control morphology of nanostructural titanates. Bavykin, D. V., et al, Adv. Mater, 2006, 18, 2807, Sun X., Li Y., Chem, Eur. J. 2003, 9, 2229 and Ma R., Sasaki T., et al., Chem. Commun 2005, 948, have demonstrated that sodium titanates nanotubes show high ion exchange reactivity towards alkali metal cations for renewable energy applications. In contrast, US Published Patent Application No. 2009/0117028 describes hydrothermal treatment methods which have longer reaction times. Hydrothermal treatment time duration varies from 10 hours to as high as 72 hours, with 24 and 48 hours being typical; however, in some cases, these extended reaction times could be impractical. Therefore, a faster synthesis is desired. In this case, microwave irradiation is considered to be the most efficient and distinct heating method, because of very short reaction time and low energy consumption needed for the reactions, compared to this conventional hydrothermal method.

V. Rodriguez-Gonzáleza, et al., J. Mol. Cat. A: Chem., 2012, 353-354, 163-170, described microwave hydrothermal treatment method for producing silver assisted titanate nanotubes. First they prepared Ag/TiO$_2$, which was mixed with 10M NaOH, followed by microwave irradiation at 150° C., 195 watts for 4 hours. After washing with 5M HCl, the resulting products were washed with water to keep pH~7 followed by drying at 95° C. for 12 hours. Their initial sample preparation method, before microwave irradiation, takes a longer time and their study did not consider microwave irradiation power, pressure, time and temperature which are the important and critical parameter in synthesizing nanotubes and nanostructured materials.

The transformation mechanism of titanate nanotubes and other nanostructured materials demonstrate insights to the structure and morphology of these materials and provide guidance to facilitate the design of nanomaterials useful for specific applications, described in US Published Patent Application No. 2009/0117028. Titanate nanotubes are usually formed by rolling nanosheets proposed by Renzhi Ma, et al., J. Phys. Chem. B 2004, 108, 2115-2119, and by B. D. Yao, et al., App. Phy. Lett., 2003, 82, 2. The references describe nanosheets formed at low temperature hydrothermal reactions and nanotube formed at higher temperature; however, formation mechanism of nanosheets from precursors are not clearly demonstrated. Jianjun Yang, et al., Dalton Trans., 2003, 3898-3901, described the combination of two theories; namely nanosheets exfoliation from the precursor or partial dissolution of precursor in concentrated sodium hydroxide solutions followed by the nucleation of sodium titanate followed by their subsequent growth. S. Zhang, et al., Phy. Rev. Lett., 2003, 91, 25, 256103-1, proposed that a mechanical tension arises during formation due to the width difference between two layers of nanosheets. In the case of structure and composition, there is some confusion. Tomoko Kasuga, et al., Langmuir, 1998, 14, 3160-3163, proposed final structure titania nanotube found by acid washing. Wenzhong Wang, et al., J. Mater. Res., 2004, 19, 2; Y. Q. Wang, et al., Chem. Phy. Lett., 2002, 365, 427-431; and G. H. Du, et al., App. Phy. Lett., 2001, 79, 22-26, proposed end product is hydrogen titanate (H$_2$Ti$_3$O$_7$) nanotubes without the need for washing. Therefore, understanding the exact mechanism of nanotube formation from nanosheets as well as their chemical structure and compositions is not clearly defined.

General interest for transition metal doping of titanate nanotubes and nanostructured materials is enormous because the surface chemistry changed by transition metal doped titanate nanostructures is a key factor to tube up the properties of catalyst and catalytic performance. Structural details related to catalytic properties and active adsorption sites in metal doped titanate nanotubes or other nanostructured materials are not yet known and required for further research. Ajayan et. al., Nature, 1995, 375, 564-567, have reported that metal oxide nanotube materials based on carbon nanotubes can be used as a template. This method contains carbon or another impurity which can be major obstacle in its application and also synthesis cost is high due to consuming template. U.S. Pat. No. 7,592,039 describes mass production of metal oxide nanotube materials but those are all of metal oxide thin film using a conventional template method.

SUMMARY

A multi-walled titanium-based nanotube array containing one or more metal or non-metal dopants is formed, in which the dopants comprise ions, compounds, clusters and particles located on at least one of a surface, inter-wall space and core of the nanotube. For a titanium-based nanotube array having multiple dopants, the dopants comprise one dopant located on the surface and a second dopant located in the inter-wall space (interlayer) of the nanotube, or one dopant located on the surface and a second dopant located in the core of the nanotube, or one dopant located on the core and a second dopant located on the inter-wall space (interlayer) of the nanotube.

The nanotubes may be prepared by providing a titanium precursor, converting the titanium precursor into titanium-based layered materials to form titanium-based nanosheets, and transforming the titanium-based nanosheets to multi-walled titanium-based nanotubes.

BRIEF DESCRIPTION OF THE DRAWINGS

FIGS. 2A-2G are photos and FIGS. 2H-2N are SEM images of different precursors. FIGS. 2O-2U are TEM images of nanosheets. FIGS. 2V-2Z are TEM images of nanotubes. FIG. 2AA shows a nanofiber product. FIG. 2AB shows a nanocomposite product.

FIGS. 4A-4H are TEM images of the titanate nanotubes. FIGS. 4A-4D are TEM images of the nanosheets prepared from pure anatase $TiO_2$ under different microwave (MW) conditions. FIGS. 4E-4H are TEM images of the titanate nanotubes prepared after washing of titanate nanosheets at different MW conditions.

FIG. 5 are TEM images of titanate nanotubes prepared under different conditions. Table 4 shows their texture structure data calculated from TEM images.

FIG. 8 is a schematic diagram of transformation mechanism from titania nanoparticles to titanate nanosheets FIG. 9 is a schematic diagram of transformation mechanism from titanate nanosheets to titanate nanotubes.

FIG. 26 is a sequence of TEM images that show that Cu/TiNT prepared from Tetraamine copper(II) nitrate (TACN), [Cu(NH3)4](NO3)2]) by different mixture methods have different morphologies.

FIGS. 28A-28C are TEM images showing different dye compound doped nanotubes, with FIG. 28D showing the nanotube arrangement of FIGS. 28A-28C.

FIG. 29 is a graphical representation of UV-V spectra resulting from band gap energy of dye doped nanotubes.

DETAILED DESCRIPTION

Overview

Figure 1:
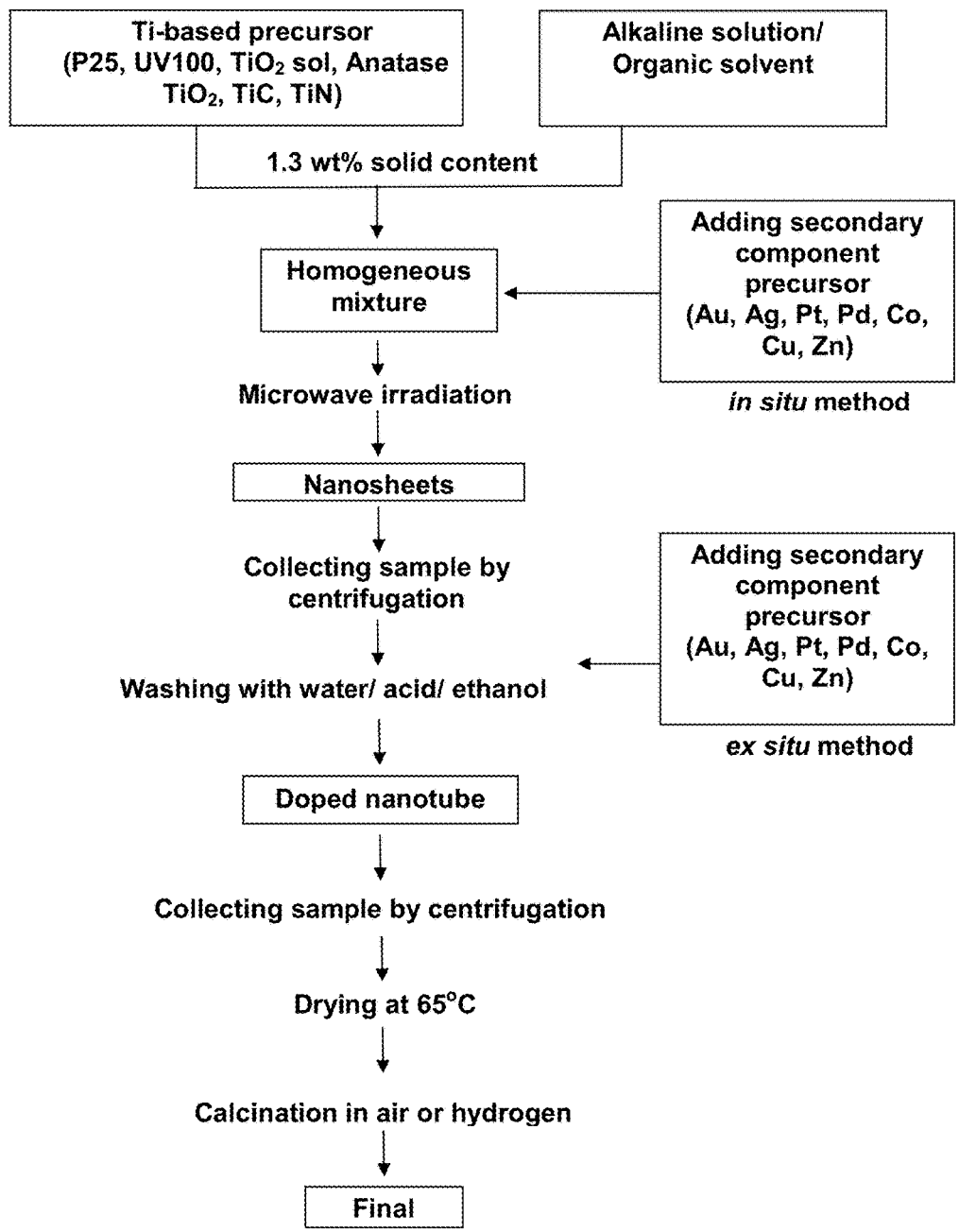
FIG. 1 is a schematic block diagram showing preparation procedures of one dimensional titanate nanomaterials from different titania precursors via in situ and ex situ techniques.

In response to the above problems, and in order to provide structural and chemical composition and transformation mechanisms of nanotubes, a synthesis technique is used for producing nanotube materials containing a transition metal/metal oxide or an organic compound by using microwave irradiation techniques of very short periods of time via two different procedures, called in situ and ex situ. Transition metal, metal oxide and compounds are incorporated into the nanotube structure on inner surfaces and between the walls of the nanotubes. According to the present disclosure, a transformation mechanism of nanotubes is provided.

The nanotubes are doped to form interlayers such that the nanotubes form a multi-walled titanium-based nanotube structure. The nanotube structure contains one or more dopants in the form of metal or non-metal ions, compounds, clusters and particles. The dopants can be applied so that a dopant layer is located on the surface of the nanotube, a dopant layer is located in the inter-wall space of the nanotube to form an interlayer and a dopant is located in the core of the nanotube. Thus, in the case of the dopant layer located in the inter-wall space of the nanotube, the dopant forms an interlayer.

The disclosed technology relates to a manufacturing method for metal doping on titanate nanostructures (nanosheets, nanotubes, nanofibers, nanocomposites) via in situ and ex situ processes based on the use of titanium precursors. Transition metals, by way of non-limiting example, $Au^{3+}$, $Ag^+$, $Pt^{2+}$, $Pd^{2+}$, $CO^{2+}$, $Cu^{2+}$, $Zn^{2+}$ are used as dopants. In particular, a different titanium precursor is used to prepare different titanate nanostructures. The effective environmental application of the prepared nanosize photocatalyst is also present.

The precursor can be prepared, by way of non-limiting example, in water, alcohol or acid solution. Non-limiting examples of alcohol are methanol, ethanol and propanol. Non-limiting examples of acids used in the acid solution are hydrochloric acid, nitric acid, sulphuric acid and acetic acid.

The technique can be implemented by transforming negatively-charged titanium-based nanosheets into multi-walled titanium-based nanotubes containing metal and/or nonmetal dopants, and transforming the positively-charged titanium-based nanosheets into multi-walled titanium-based nanotubes containing a metal and/or non-metal dopants. This is accomplished by rinsing the nanosheets with an anionic or cationic solution of a precursor for the dopant according to whether the nanosheets transformed are negatively or positively charged.

For transforming the transforming negatively charged titanium based nanosheets into multi walled titanium based nanotubes containing metal and/or non metal dopants by single, sequential or combination by combination, the transforming the negatively charged titanium based nanosheets, the process comprises:
  a. rinsing the titanium based nanosheets in a solution of a concentrated anionic precursor for the dopant to obtain multi walled titanium based nanotubes with dopants on the surface;
  b. rinsing the titanium based nanosheets in a solution of a cationic precursor for the dopant to obtain multi walled titanium based nanotubes with dopants in the inter wall spaces (interlayer);
  c. rinsing the titanium based nanosheets in a solution of the dilute anionic precursor for the dopant to obtain multi walled titanium based nanotubes with dopants in the core, or,
  a. rinsing with water or acid solution to obtain multi walled titanium based nanotubes containing metal and/ or nonmetal dopants;
  b. rinsing with a concentrated anionic solution of a precursor for a dopant to introduce additional dopant on surface;
  c. rinsing with a cationic solution of a precursor for a dopant to introduce additional dopant in the inter wall space (interlayer);
  d. rinsing with a dilute anionic solution of a precursor for a dopant to introduce additional dopant in the core.

For transforming the transforming the positively charged titanium based nanosheets into multi walled titanium based nanotubes containing a metal and/or non metal dopants by single, sequential or combination, the transforming the positively charged titanium based nanosheets, the process comprises:
  a. rinsing the titanium based nanosheets in a solution of the concentrated cationic precursor for the dopant to obtain multi walled titanium based nanotubes with dopants on the surface;
  b. rinsing the titanium based nanosheets in a solution of the anionic precursor for the dopant to obtain multi walled titanium based nanotubes with dopants in the inter wall spaces (i.e., interlayer);
  c. rinsing the titanium based nanosheets in a solution of the dilute cationic precursor for the dopant to obtain multi walled titanium based nanotubes with dopants in the core, or,
  a. rinsing with water or acid solution to obtain multi walled titanium based nanotubes containing metal and/ or nonmetal dopants;
  b. rinsing with a concentrated cationic solution of a precursor for a dopant to introduce additional dopant on surface;
  c. rinsing with a anionic solution of a precursor for a dopant to introduce additional dopant in the inter wall space (interlayer);
  d. rinsing with a dilute cationic solution of a precursor for a dopant to introduce additional dopant in the core.

Titanium nanomaterials comprise a metal or metal oxide with one dimensional nanostructures, or nanomaterials comprising a composite material of an inorganic or organic compound and a metal oxide having nanotube structures, have been found to have different physical and chemical properties from the corresponding bulk materials, and are consequently attracting adequate interest in fundamental research as well as applied research. In particular elongated hollow nanotube materials composed of metal/metal oxides and the inorganic/organic compounds are expected to be applied in a wide variety of fields, such as catalysis, electrocatalysis, photocatalysis, renewable energy, hydrogen storage and sensing, magnetic material, antibacterial, biomedicine, separation technology, inclusion chemistry, electrochemistry and other uses.

The metal oxide dopant may, by non-limiting example, be obtained by heat treatment in oxidizing atmosphere of air, oxygen or ozone. The metal dopant may also, by non-limiting example, be obtained by heat treatment in reducing atmosphere of hydrogen and carbon monoxide.

One dimensional Ti-based nanomaterials (nanosheet, nanotube, nanofiber and nanocomposite (0D nanoparticles and 1D nanotubes)) with controlled doping either on the core, interlayer and outer surfaces of the nanotubes are prepared by a simple microwave process. After microwave irradiation precursors convert to nanosheets. Further washing treatments, nanosheets transform to nanotubes and incorporated target dopants. Dopants could be atoms or clusters of metals, metal oxides, alloys and organic compounds.

Ti-based nanomaterials have great potential applications. Transition metal doped nanotubes have good adsorption & photocatalytic oxidation performances of endocrine disrupting compounds (EDCs), organic pollutants and dyes in water under both visible and UV light irradiation. Some metal doped titanate nanotubes show 90~100% dye degradation, 91% DCP degradation under visible light and 100% diclofenac adsorption.

In particular, the disclosed technology provides a standard method for manufacturing different titanate nanostructures from various titanium sources. The numerous titanium precursor can include, without limitation, anatase $TiO_2$, P-25, UV 100, modified sol-gel $TiO_2$, Titanium nitride (TiN), or Titanium carbide (TiC).

Process

The process includes:

Sample Preparation:

Microwave (MW) hydrothermal irradiation method

Post synthesis treatment of titanate nanomaterials

Further treatment of titanate nanomaterials

Formation mechanism of titanate nanotube

Application of the Titanate Nanotubes:
Adsorption of endocrine disrupting compound (EDC),
Photocatalytic activity for dye and organic pollutants under visible and UV light irradiation,
Disinfection of bacteria (*S. aureus*).

Titanate nanotube transformation from nanosheets is involved as a driving force. This driving force occurs during post synthesis washing.

FIG. 1 is a schematic block diagram showing preparation procedures of one dimensional titanate nanomaterials from different titania precursors via in situ and ex situ techniques. The difference between two techniques is the addition order of the precursors of metals, metal oxides and organic compounds.

Figure 2A:
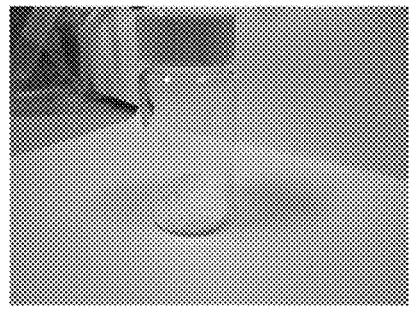
FIGS. 2A-2AB are images of precursors and products produced by the in situ and ex situ techniques.
Figure 2B:
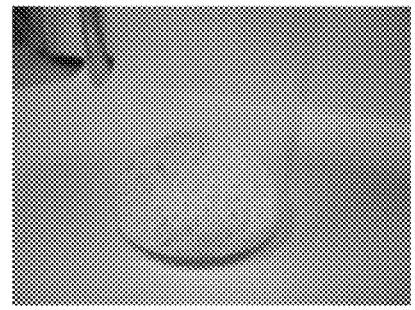
Figure 2C:
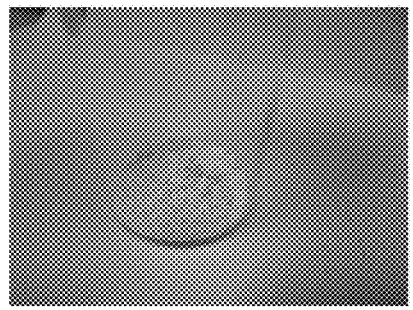
Figure 2D:
Figure 2E:
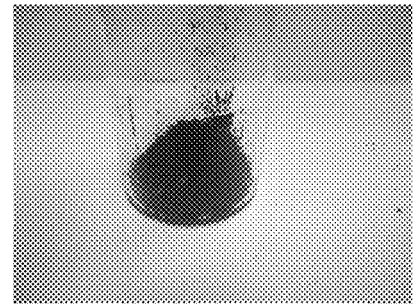
Figure 2F:
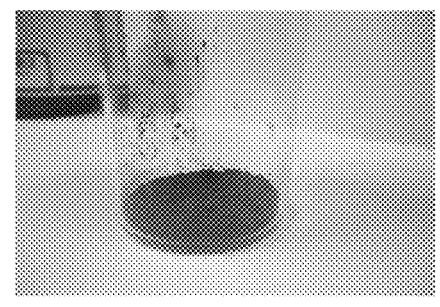
Figure 2G:
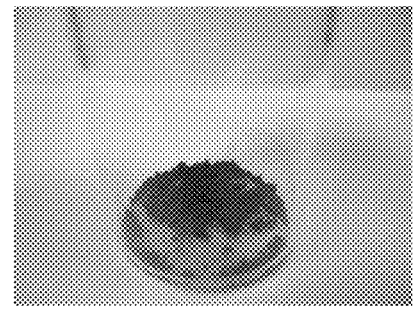
Figure 2H:
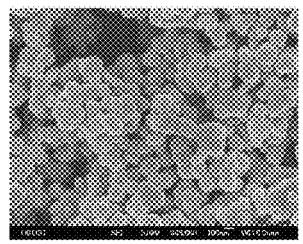
Figure 2I:
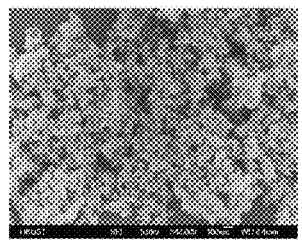
Figure 2J:
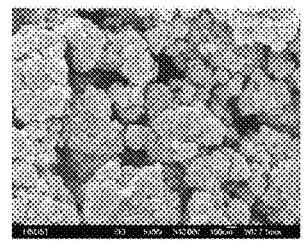
Figure 2K:
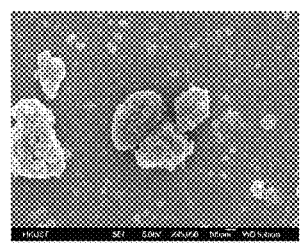
Figure 2L:
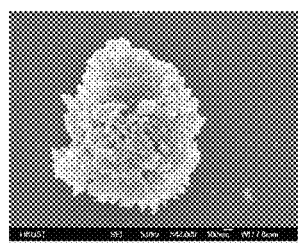
Figure 2M:
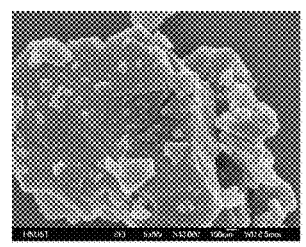
Figure 2N:
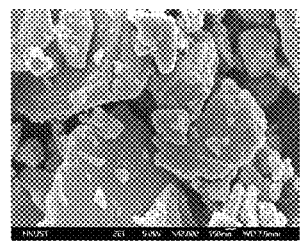
Figure 2O:
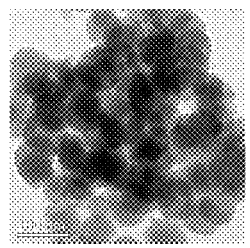
Figure 2P:
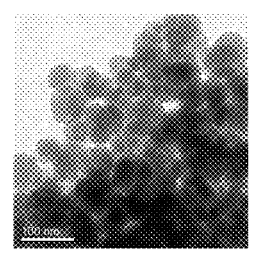
Figure 2Q:
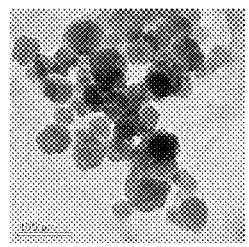
Figure 2R:
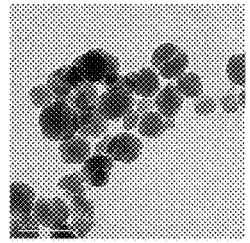
Figure 2S:
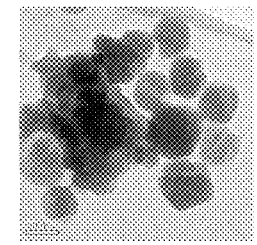

FIGS. 2A-2U are images of precursors and products produced by the in situ and ex situ techniques. FIGS. 2A-2G are photos. FIGS. 2H-2N are SEM images of different precursors. FIGS. 2O-2U are TEM images of nanosheets. FIGS. 2V-2Z are TEM images of nanotubes. FIG. 2AA shows a nanofiber product. FIG. 2AB shows a nanocomposite product.

The nanofiber product (FIG. 2AA) and nanocomposite product (FIG. 2AB are prepared from different precursors:
(FIG. 2A, FIG. 2H, FIG. 2O, and FIG. 2V) pure anatase $TiO_2$;
(FIG. 2B, FIG. 2I, FIG. 2P, FIG. 2W) P25;
(FIG. 2C, FIG. 2J, FIG. 2Q, FIG. 2X) UV 100;
(FIG. 2D, FIG. 2K, FIG. 2R, FIG. 2Y) $TiO_2$ solution;
(FIG. 2E, FIG. 2L, FIG. 2S, FIG. 2Z), calcined TiC at 350° C. for 2 hr;
(FIG. 2F, FIG. 2M, FIG. 2T, FIG. 2AA), TiC;
(FIG. 2G, FIG. 2N, FIG. 2U, FIG. 2AB) TiN.

The different titania precursors are shown in FIGS. 2A-2H. After microwave treatment these titania precursors transformed into titanate nanosheets. FIG. 2 (O-U) show that titanate nanosheets have multilayer morphology. After washing, titanate nanosheets can be changed into titanate nanotubes, nanofiber or nanocomposites (0D nanoparticles and 1D nanotubes) depending on different precursors. Nanotubes have long cylindrical shapes with the aspect ratio (length to diameter) of 10 to 150. Nanofibers have larger aspect ratio of several thousand. There is a co-existence of 1D nanotubes and 0D nanoparticles within nanocomposites.

Figure 3:
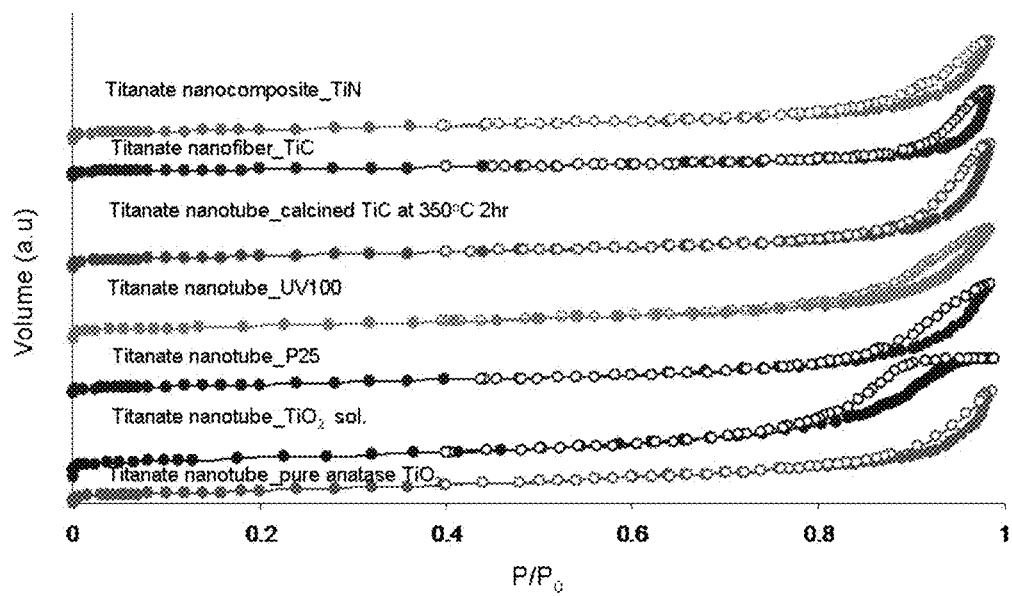
FIG. 3 is a sequenced series of graphic depictions of $N_2$ adsorption-desorption isotherms of titanate nanotubes.

FIG. 3 is a sequenced series of graphic depictions of $N_2$ adsorption-desorption isotherms of titanate nanotubes (FIG. 2 V-AB) prepared from different precursors shown in FIGS. 2A-2G using MW irradiation at 180° C. for 90 min. Their isotherms can be attributed to Type IV which indicates titanate nanotubes are mesoporous materials. Table 1 shows porous structure data calculated from isotherm of titanate nanotubes.

TABLE 1

| Titania Precursors | $S_{BET}$ (m$^2$/g) | $V_{Total}$ (cm$^3$/g) | $V_{Micro}$ (cm$^3$/g) | $D_{Micro}$ (nm) | $D_{Meso}$ (nm) |
|---|---|---|---|---|---|
| Pure Anatase $TiO_2$ | 293 | 1.19 | 0.13 | 0.6 | 11.4 |
| P25 | 197 | 0.90 | 0.08 | 0.7 | 12.6 |
| UV-100 | 268 | 0.92 | 0.12 | 0.7 | 6.1 |
| $TiO_2$ Sol. | 353 | 1.00 | 0.16 | 0.6 | 8.5 |
| Calcined TiC at 350° C. for 2 hr | 221 | 0.96 | 0.10 | 0.7 | 9.0 |
| TiC | 130 | 0.66 | 0.06 | 0.6 | 8.7 |

Sample Preparation:
Homogeneous $TiO_2$ Mixture Preparation:
Sample preparation includes the following steps except where noted:

Titanium di-oxide ($TiO_2$) is mixed with high concentrated sodium hydroxide (NaOH) or Potassium hydroxide (KOH) or mixed of NaOH and tetramethylammonium hydroxide (TMAOH) at a molar ratio of 1:1 or an organic solvent: Glycerol or Ethylene Glycol (EG) and stirring for about 2 to 3 hours in room temperature until a homogeneous, clear solution is obtained. A homogeneous solution is made herein.

For in situ metal doping, a definite amount of metals is added into the above mixture and again stirring for 2 to 3 hours in dark environment i.e., container may aluminum wrapping or keep in a box. A homogeneous solution is made herein.

b) Microwave (MW) Hydrothermal Irradiation Method:

The above homogeneous mixture is then doing microwave hydrothermal irradiation at 180° C. to 195° C. for 30 to 360 minutes. Using continuous or pulse microwave hydrothermal process enables easy, rate enhancement and reproducibility of nanomaterials. The as-prepared sample is referred to as MW treated sample, and more specifically is referred to as nanosheets. This step is the precursor of nanotubes. In case of metal doping, MW treated sample is designated as metal doped nanosheets.

FIGS. 4A-4H are TEM images of the titanate nanotubes. FIGS. 4A-4D are TEM images of the nanosheets prepared from pure anatase $TiO_2$ under different MW conditions. FIGS. 4E-4H are TEM images of the titanate nanotubes prepared after washing of titanate nanosheets at different MW conditions.

FIGS. 4A-4D are TEM images of the nanosheets prepared from pure anatase $TiO_2$ under MW conditions of: (4A) 180° C., 30 min, rendering an average diameter of 46-60 nm; (4B) 180° C., 90 min, rendering an average diameter of 45-55 nm; (4C) 180° C., 360 min, rendering an average diameter of 59-86 nm; and (4D) 195° C., 90 min, rendering an average diameter of 30-51 nm. The average diameter of the nanosheets increases with the increase of irradiation time and temperatures.

TABLE 2

| MW Condition | $S_{BET}$ (m$^2$/g) | Avg. dia (nm) |
|---|---|---|
| 180° C.-30 min | 8 | 46~60 |
| 180° C.-90 min | 4 | 45~55 |
| 180° C.-360 min | 3 | 59~86 |
| 195° C.-90 min | 5 | 30~51 | c) Post Synthesis Treatment of Titanate Nanomaterials
1) For the homogeneous mixture a.1 and a.2 (of the sample preparation part): After MW hydrothermal irradiation, nanosheets or metal doped nanosheets are washed with aqueous solution for preparing 1D titanate nanomaterial incorporated by metal precursors and organic compounds.
2) For ex situ metal doping, a definite amount of aqueous solution containing metal precursors and organic compounds is mixed with MW treated sample and stirring for 2 to 3 hours in dark environment. The doped titanate nanotubes are collected using centrifugation.

FIGS. 4E-4H are TEM images of the titanate nanotubes prepared after washing of titanate nanosheets at MW conditions of (4E) 180° C., 30 min; (4F) 180° C., 90 min; (4G) 180° C., 360 min and (4H) 195° C., 90 min. Table 3 shows the texture structure data of titanate nanotubes calculated from TEM results. Brunauer-Emmett-Teller (BET) surface area and wall number of the nanotubes increases gradually with the increase of MW irradiation time while elevated temperature results in the decrease of BET surface area and wall number.

TABLE 3

| MW Condition | $S_{BET}$ (m$^2$/g) | Avg. length (nm) | I.D (nm) | O.D (nm) | No. of wall | Interlayer tube spacing (nm) |
|---|---|---|---|---|---|---|
| 180° C.- 30 min | 209 | 55~400 | 5.7 | 12.1 | 4~5 | 0.7 |
| 180° C.- 90 min | 293 | 70~250 | 4.2 | 9.42 | 5~6 | 0.6 |
| 180° C.- 360 min | 316 | 80~600 | 3.3 | 10.6 | 7~8 | 0.5 |
| 195° C.- 90 min | 215 | 450~600 | 3.1 | 7.21 | 3~4 | 0.7 |

FIG. 5 are TEM images of titanate nanotubes prepared under different conditions. FIG. 5A shows the results of preparation using MW solvent NaOH (10M), with an acid washing solvent. FIG. 5B shows the results of preparation using MW solvent NaOH (10M), achieved by washing with double de-ionized (DDI) water at room temperature. FIG. 5C shows the results of preparation using MW solvent NaOH (10M), achieved by washing with double de-ionized (DDI) water at 80° C. FIG. 5D shows the results of preparation using MW solvent NaOH (10M), with ethanol (absolute≥99.9%). FIG. 5E shows the results of preparation using MW solvent NaOH (10M), with ethylene glycol. FIG. 5F shows the results of preparation using MW solvent NaOH (10M), with glycerol. FIG. 5G shows the results of preparation using MW solvent NaOH (10M), with KOH (10M). FIG. 5H shows the results of preparation using MW solvent NaOH (10M), with NaOH and TMAOH molar ratio (1:1).

Table 4 shows their texture structure data calculated from TEM images.

TABLE 4

Figure 6A:
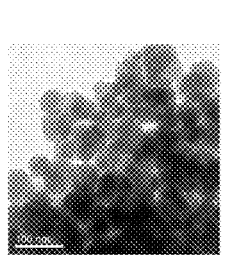
FIGS. 6A-6H are a series of TEM images depicting a sequence of transformation from nanosheets.
Figure 6B:
Figure 6C:
Figure 6D:
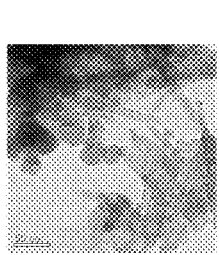
Figure 6E:
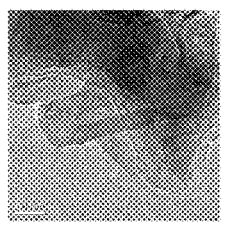
Figure 6F:
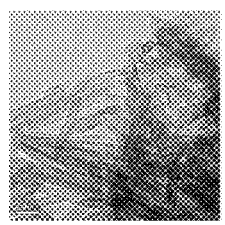
Figure 6G:
Figure 6H:
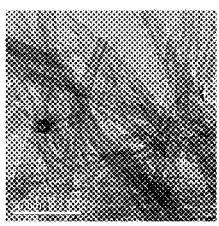

| Solvent | Washing Solution | Avg. length (nm) | I.D (nm) | O.D (nm) | No. of wall | Interlayer tube spacing (nm) |
|---|---|---|---|---|---|---|
| NaOH (10M) | 0.1M HCl | 55~400 | 5.7 | 12.1 | 4~5 | 0.7 |
| | DDI at room temp. | 56~410 | 5.7 | 11.4 | 4~5 | 0.7 |
| | DDI at 80° C. | 55~260 | 4.4 | 10.5 | 4~5 | 0.7 |
| | Ethanol (absolute ≥99.9%) | 70~500 | 5.3 | 11.3 | 3~4 | 0.8 |
| Ethylene Glycol (EG) | Ethanol (absolute ≥99.9%) | 105~615 | 5.1 | 12.3 | 5~6 | 0.6 | d) Formation Mechanism of Titanate Nanotube:

FIGS. 6A-6H are a series of TEM images depicting a sequence of transformation from nanosheets. Titanate nanotube transformation from nanosheets is involved some driving force. This driving force is happened during post synthesis washing, as shown in FIGS. 6a-6c). The post synthesis are depicted in the sequence shown in FIGS. 6A-F. In FIG. 6A, $Na_2Ti_nO_{2+1}$ is shown after microwave treatment. In FIGS. 6B and 6C, the structure is shown after washing for 1 minute. In FIGS. 6D and 6E, the structure is shown after washing for 2 minutes. In FIG. 6F, the structure is shown after washing for 40 minutes. In FIG. 6H, the structure is shown after washing for 70 minutes. The final structure (e.g., in FIG. 6F) is $H_2Ti_nO_{2n+1}$.

Figure 7A:
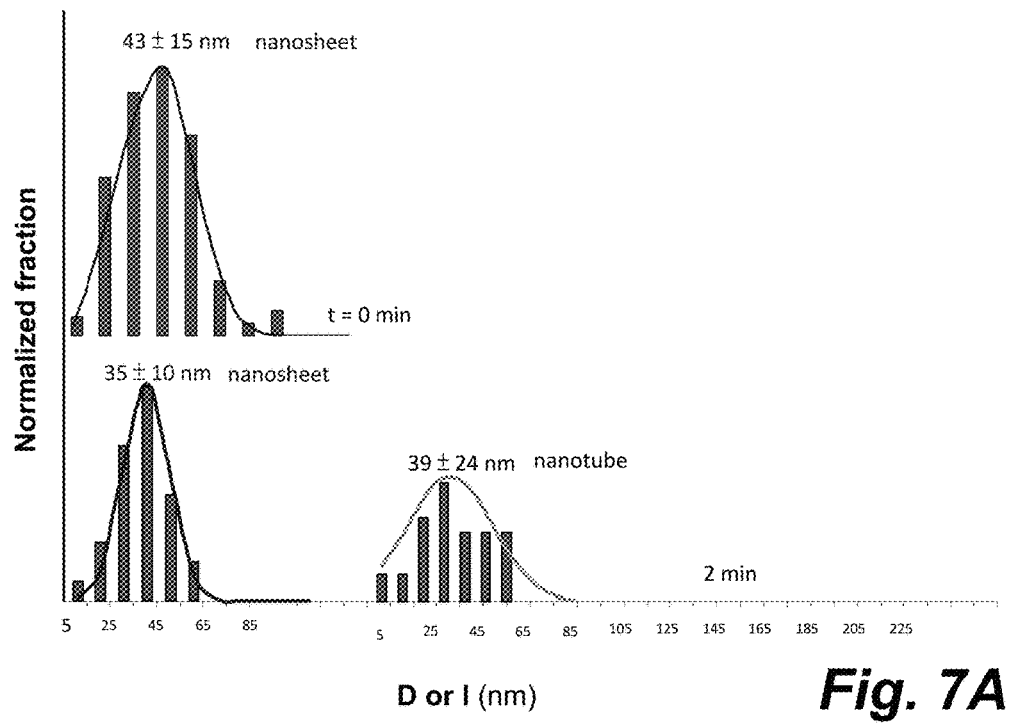
FIGS. 7A and 7B are a series of graphs showing particle size distribution (PSD) of titanate nanotubes, prepared from titanate nanosheets, calculated from TEM morphology in FIG. 6.
Figure 7B:
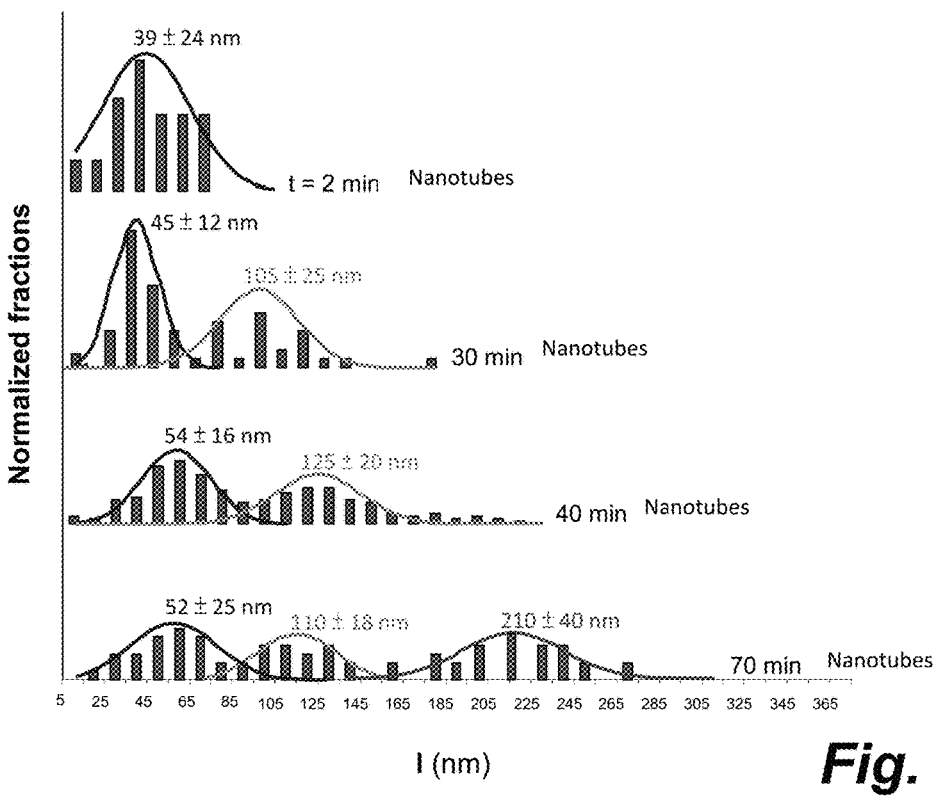

FIGS. 7A and 7B are a series of graphs showing particle size distribution (PSD) of titanate nanotubes, prepared from titanate nanosheets, calculated from TEM morphology in FIG. 6.

After exposure to moisture or aqueous solution, ion exchange occurs to form Ti—OH moiety. Within two minutes, are observed thin sheets with different curvatures and short tubes (FIG. 6C and FIG. 7A). More tube appear from sheets after 30 minutes FIG. 6D. Short nanotubes attach together to form longer nanotubes.

Figure 8:
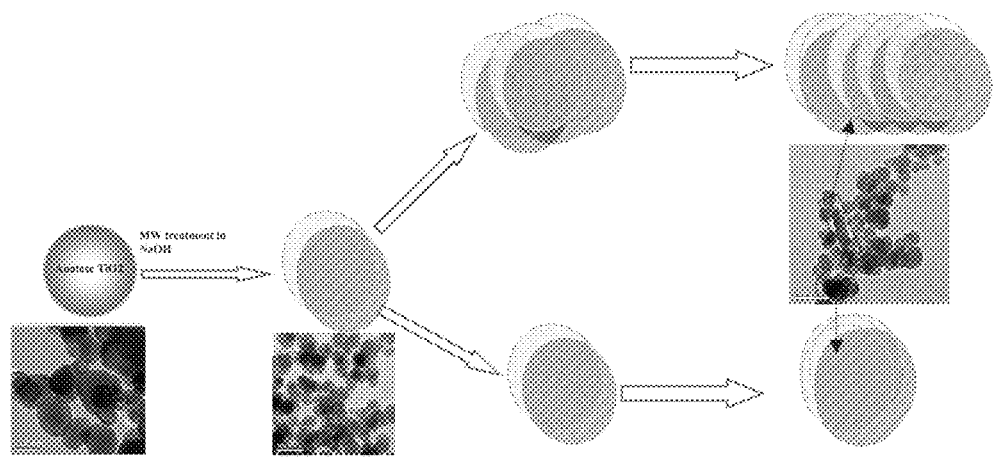
FIGS. 8-9 are schematic diagrams of a transformation mechanism.
Figure 9:
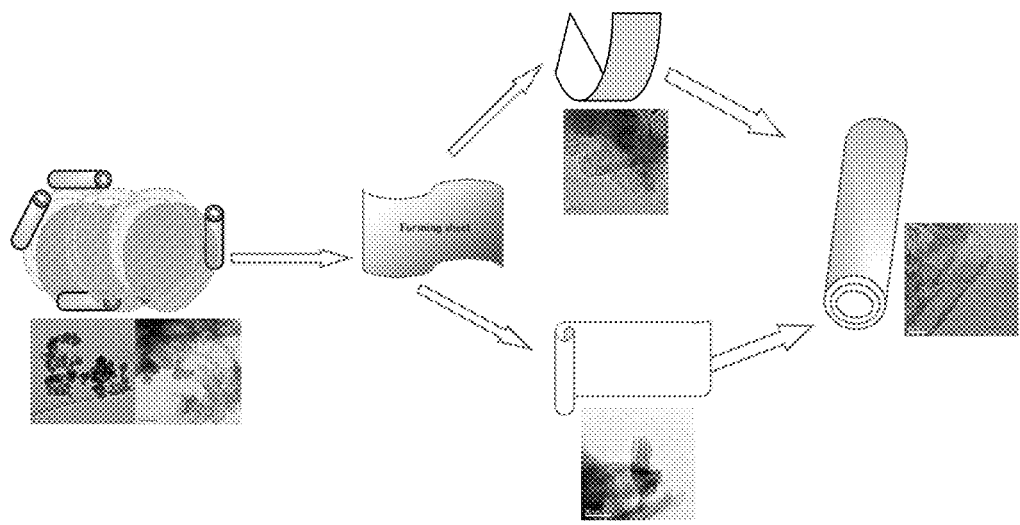

According to above mentioned experimental results, a three-stage mechanism is proposed. FIGS. 8-9 are schematic diagrams of a transformation mechanism. FIG. 8 is a schematic diagram of transformation mechanism from $TiO_2$ (titania) nanoparticles to titanate nanosheets. Anatase $TiO_2$ nanoparticles are subjected to MW treatment in NaOH. The material is transformed into titanate nanosheets.

In FIG. 9 the titanate nanosheets are transformed to titanate nanotubes. The transformation mechanism is:
1) Globular like nanosheets, sodium titanate structured are formed at the primary stage of alkaline microwave treatments.
2) Post treatment washing, nanosheets are exfoliated.
3) Curling and scrolling of exfoliated sheets lead to nanotube formation and short nanotubes connect together to form longer nanotubes.

Figure 10:
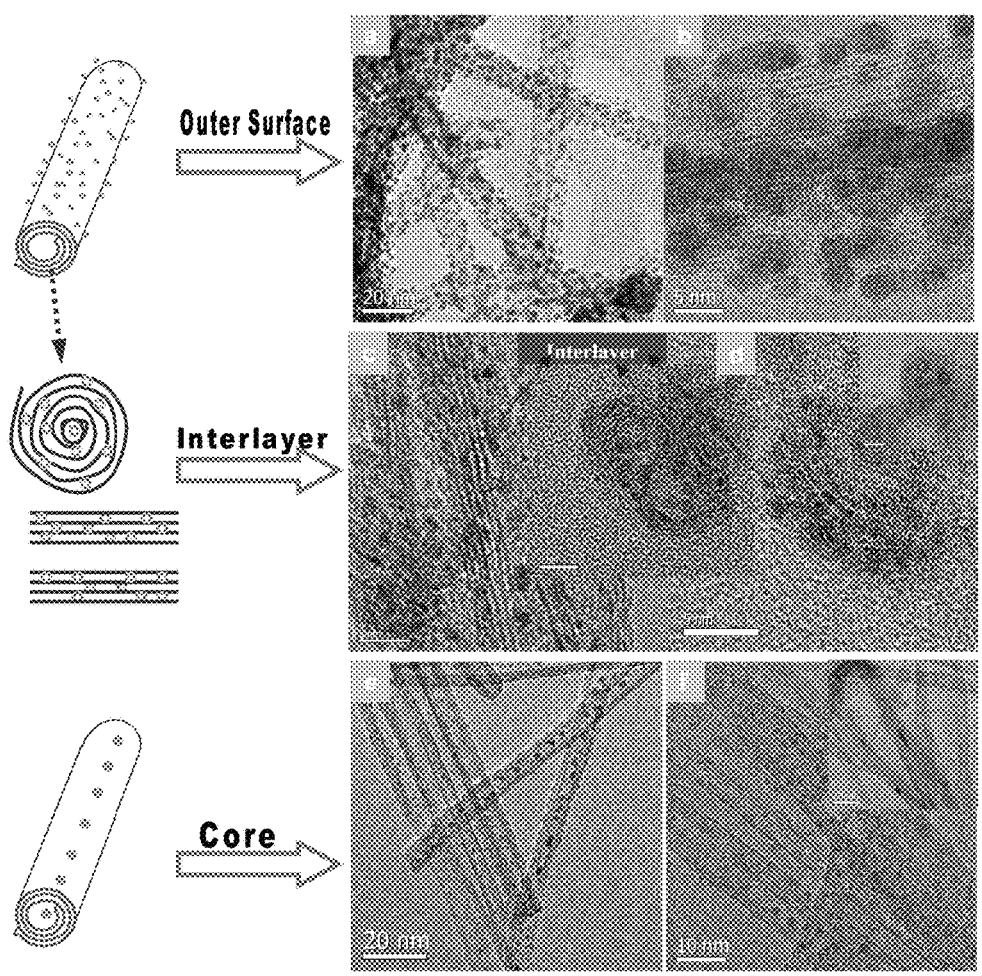
FIG. 10 is a sequenced series of TEM images of Au/TiNT with different morphologies prepared from different gold precursors.

FIG. 10 is a sequenced series of TEM images of Au/TiNT with different morphologies prepared from different gold precursors. Gold elements are doped on the outer surfaces, interlayer and on the core of the nanotubes by using hydrogen tetrachloroaurate (III) trihydrate ($HAuCl_4 \cdot 3H_2O$) and Tetraamine gold (III) nitrate, $[Au(NH_3)_4](NO_3)_3$ as precursors respectively. From Table 5, doped samples present decreased BET surface area compared to titanate nanotubes.

Figure 11:
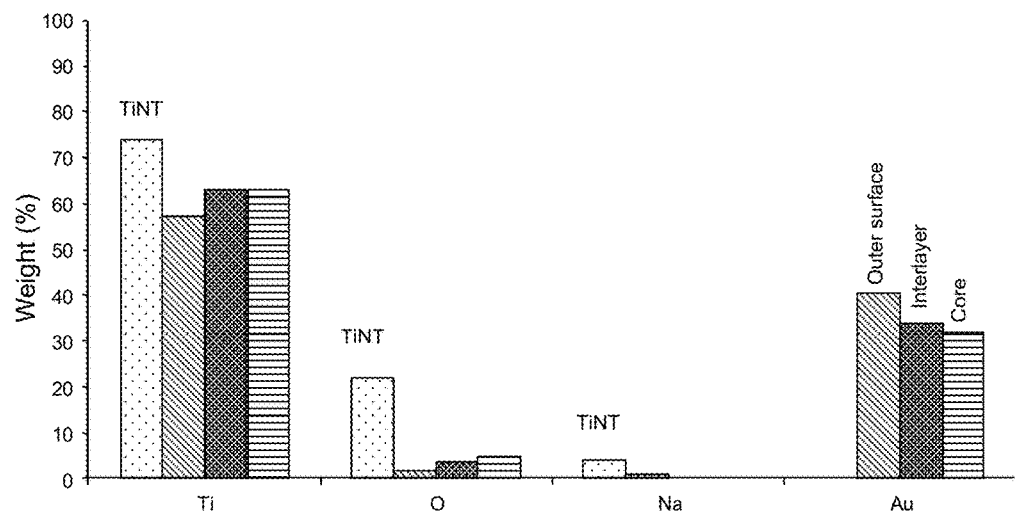
FIG. 11 is a graphical depiction of an EDX quantitative analysis. The EDX quantitative analysis provides verification of the existence of gold elements.

FIG. 11 is a graphical depiction of an EDX quantitative analysis of Au/TiNT. The EDX quantitative analysis provides verification of the existence of gold elements.

TABLE 5

| Name of the catalyst | $S_{BET}$ (m$^2$/g) | $V_{Total}$ (cm$^3$/g) |
|---|---|---|
| TiNT | 293 | 1.19 |
| Gold (III) doped TiNT | 169 | 0.55 |
| Gold (III) complexes doped TiNT | 141 | 0.88 |

Figure 12:
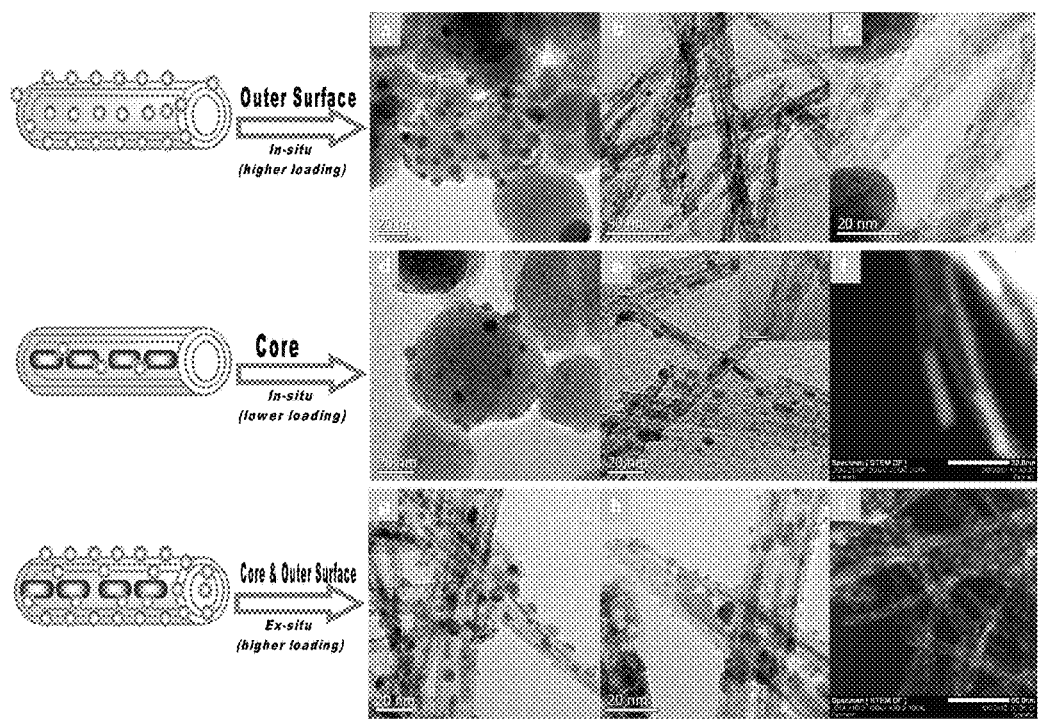
FIG. 12 is a sequenced series of TEM images of Ag/TiNT with different morphologies prepared from silver precursor (AgNO3).
Figure 13:
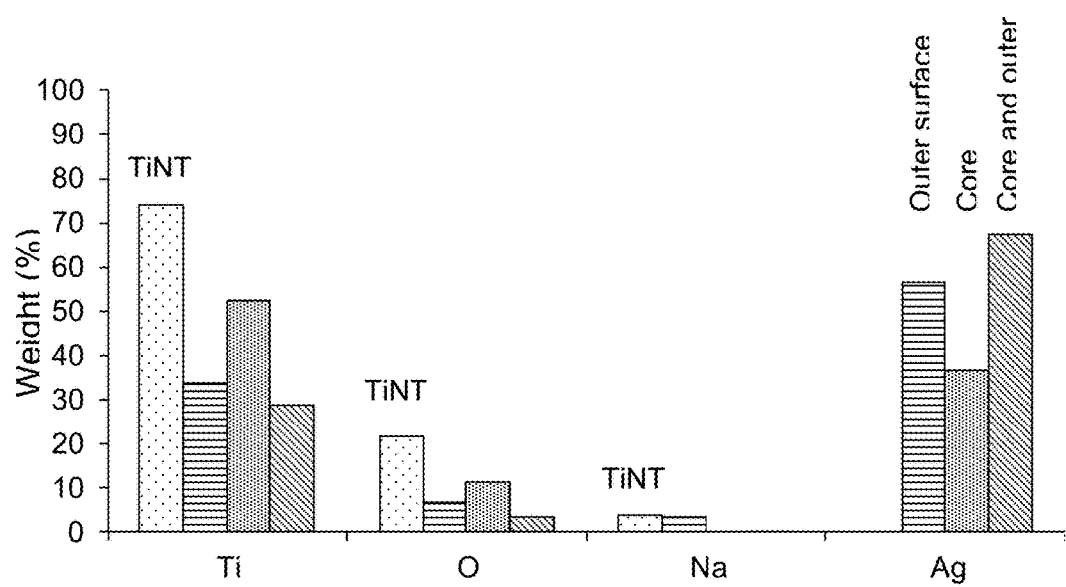
FIG. 13 is a graphic depiction of an EDX quantitative analysis.
Figure 14:
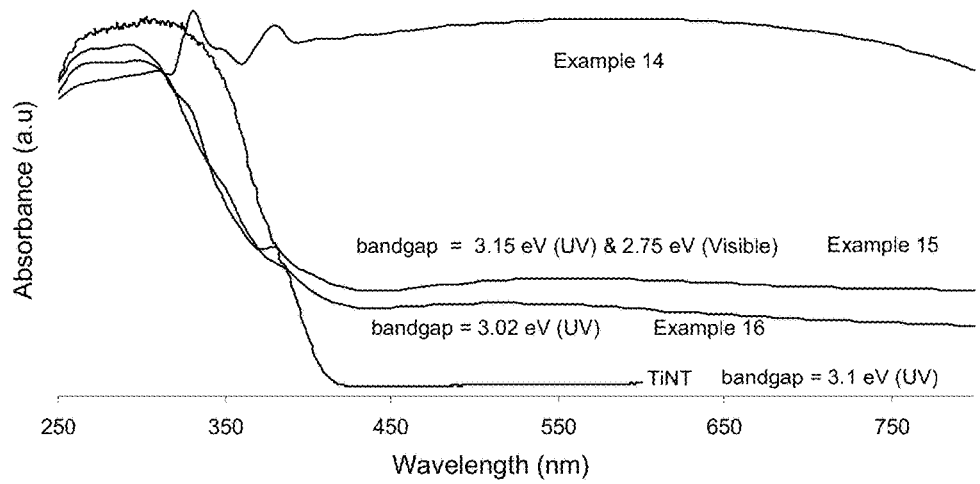
FIG. 14 is a graphical depiction of band gap energy of Ag/TiNT calculated from UV-Vis spectra.
Figure 15:
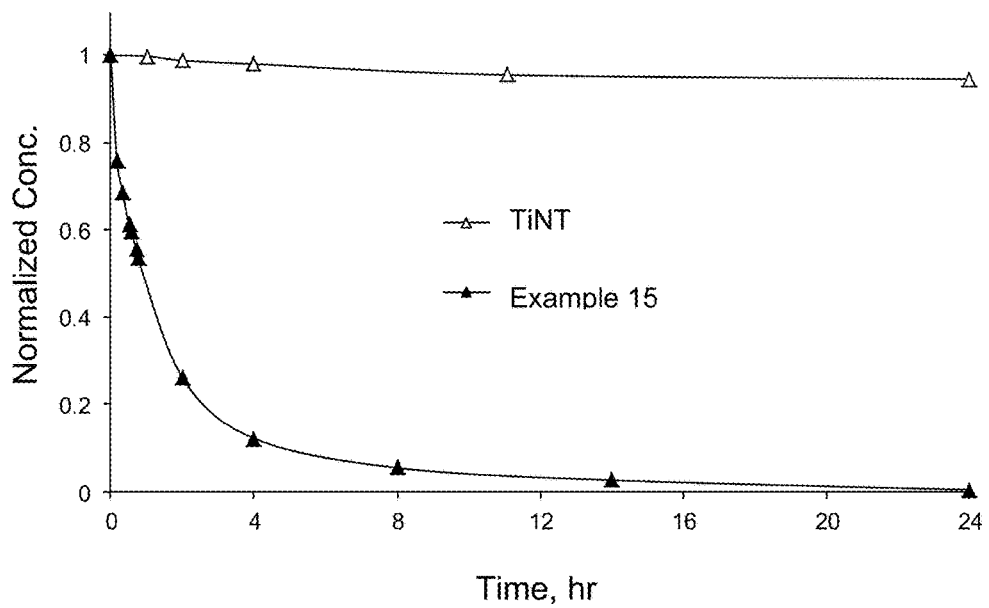
FIG. 15 is a graphic depiction showing adsorption performance of TiNT and Ag/TiNT via in situ techniques.

FIG. 12 is a sequenced series of TEM images of Ag/TiNT with different morphologies prepared from silver precursor ($AgNO_3$). Silver elements are doped on the outer surfaces, core and both outer surfaces and core via in situ and ex situ techniques. FIG. 13 is a graphic depiction of an EDX quantitative analysis. The depiction of FIG. 13 verifies the existence of silver elements. FIG. 14 is a graphical depiction of band gap energy of Ag/TiNT calculated from UV-Vis spectra. The depiction of FIG. 14 presents sample prepared via in situ have both visible and UV spectrum. Ex situ sample shows absorbance in full wavelength ranges.

e) Application of
1) Adsorption of endocrine disrupting compound (EDC)
2) Photocatalytic activity for dye (methylene blue) and organic pollutant (2,4 dichlorophenol) under visible and UV light irradiation.
3) Disinfection of bacteria (S. aureus) from a liquid Adsorption of Endocrine Disrupting Compound (EDC):

Ag/TiNT has a very good adsorption capacity compared to TiNT. FIG. 15 is a graphic depiction showing adsorption performance of TiNT and Ag/TiNT via an in situ technique for diclofenac (DFS).

Photocatalytic Oxidation:

The photo degradation experiments were performed for different titanate nanotubes & metal doped nanotubes prepared from different precursors. The photocatalytic activities of the samples (0.2 g/L of photocatalyst) were tested by the decomposition of dye and organic pollutant (100 mL with initial concentration 0.1 g/L). Prior to irradiation, the sample were stirred for 1 to 24 hr to establish an adsorption-desorption equilibrium. The photocatalytic reactor were carried out under visible (e.g., 500 W high pressure mercury lamp or 250 W metal halide lamp) and UV light (6 W UV lamp with the wavelength 315 nm-400 nm). The concentration of dyes and organic pollutants were detected by HPLC or UPLC.

Figure 16:
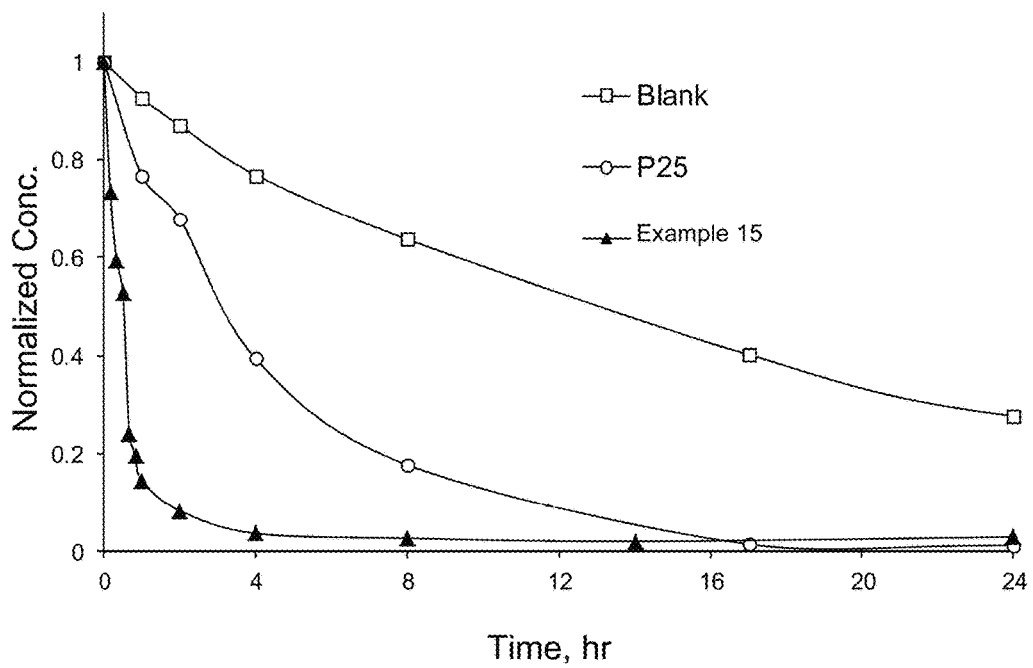
FIG. 16 is a graphic depiction showing photocatalytic activity of Ag/TiNT via in situ techniques under UV light irradiation.

FIG. 16 is a graphic depiction showing photocatalytic activity of Ag/TiNT via in situ techniques. This results in higher performance compared to P25 dichlorophenol for methylene blue (MB) oxidation under UV light. The top line shows results for no dye (open squares). The middle line shows results for P25 (open circles). The lower line shows results for methylene blue (triangles).

Figure 17:
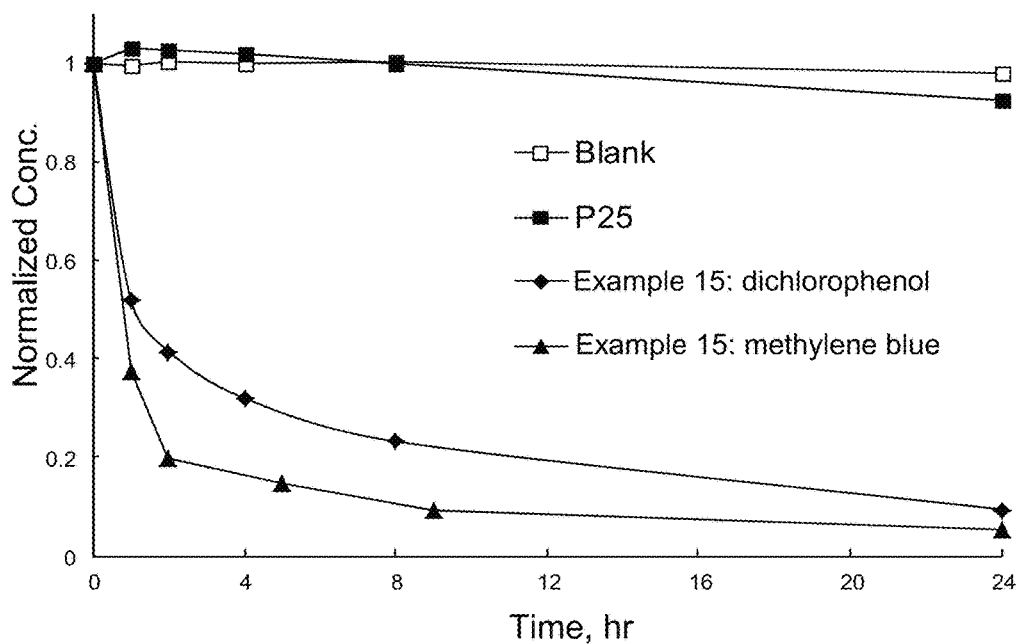
FIG. 17 is a graphic depiction showing photocatalytic activity of Ag/TiNT via in situ techniques under visible light irradiation.

FIG. 17 is a graphic depiction showing photocatalytic activity of Ag/TiNT via in situ techniques. The top lines show similar results for no dye (open squares) and P25 (filled squares). The lower lines show results for dichlorophenol (diamonds), and methylene blue (triangles; lowermost line). Referring to FIG. 17, it was found that this process provides higher performance as compared to P25 dichlorophenol for 2,4-dichlorophenol (DCP) and methylene blue (MB) oxidations under visible light.

Figure 18:
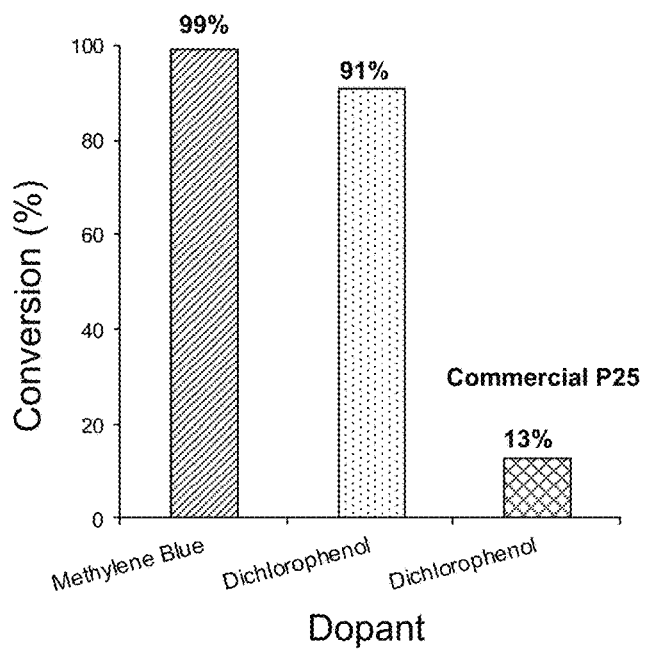
FIG. 18 is a graphical representation of calculated conversion of 2,4-dichlorophenol (DCP), methylene blue (MB) on Ag/TiNT via in situ techniques and commercial P25 under visible light irradiation.

FIG. 18 is a graphical representation of calculated conversion of 2,4-dichlorophenol (DCP), methylene blue (MB) on Ag/TiNT via in situ techniques and commercial P25 dichlorophenol under visible light irradiation.

Figure 19:
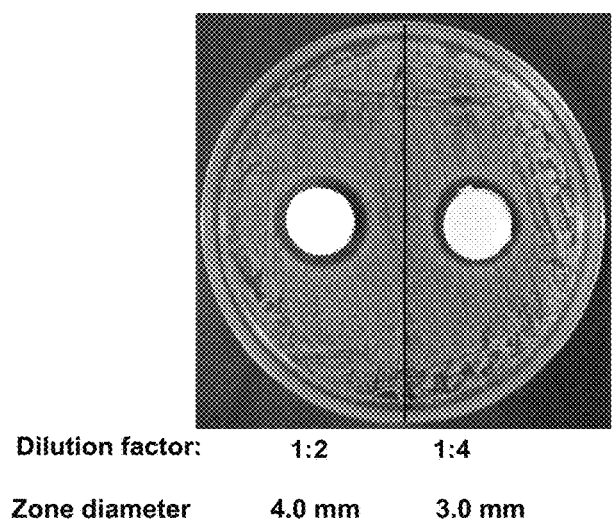
FIG. 19 is a photographic image showing inhibition zones of Ag/TiNT achieved via in situ techniques for $10^4$ CFU/ml S. aureus.

Disinfection from Bacteria (*S. aureus*):

99% disinfections from *S. aureus* (FIG. 19) are found using transition metal doped nanotubes. The left side shows a dilution factor of 1:2 over a zone diameter of 4.0 mm. The right side shows a dilution factor of 1:4 over a zone diameter of 3.0 mm.

Figure 20:
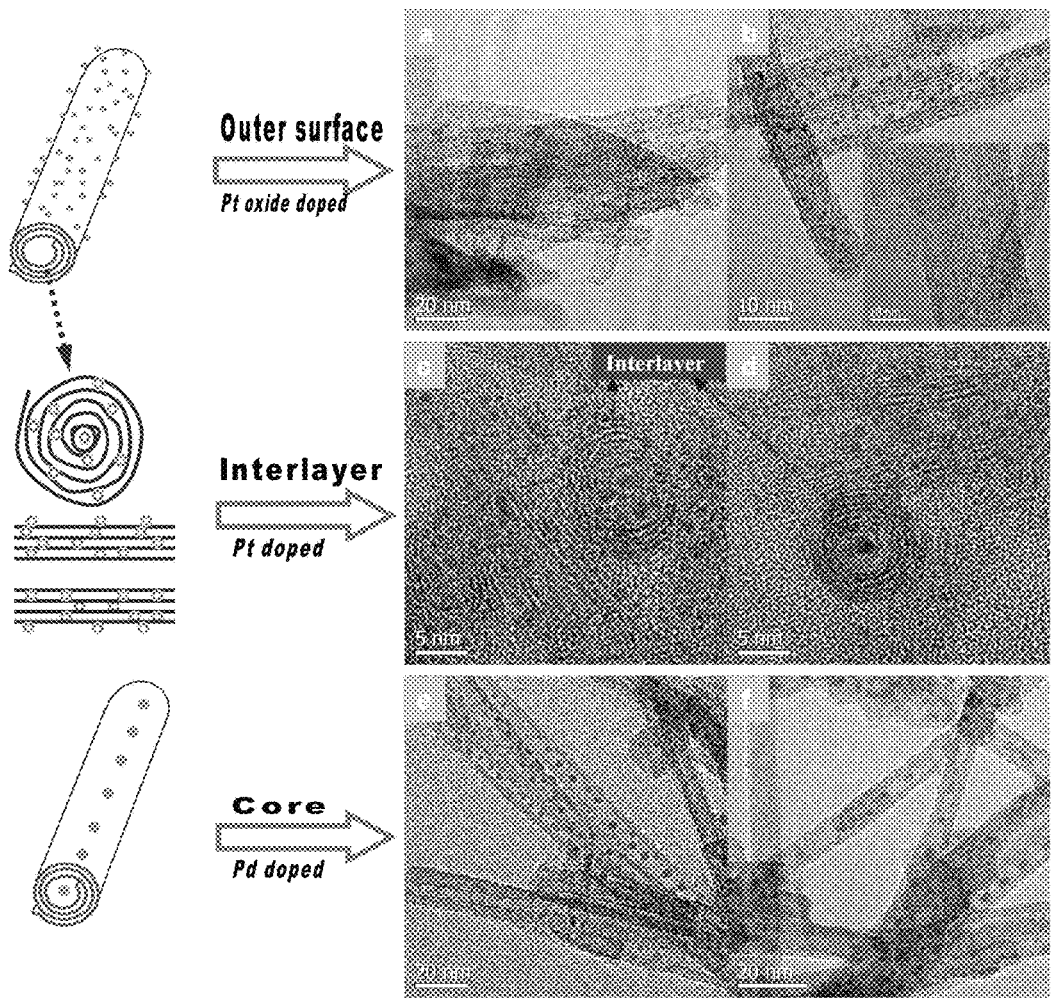
FIG. 20 is a sequenced series of Pt/TiNT with different morphologies, with a schematic representation of the core and interlayer.
Figure 21:
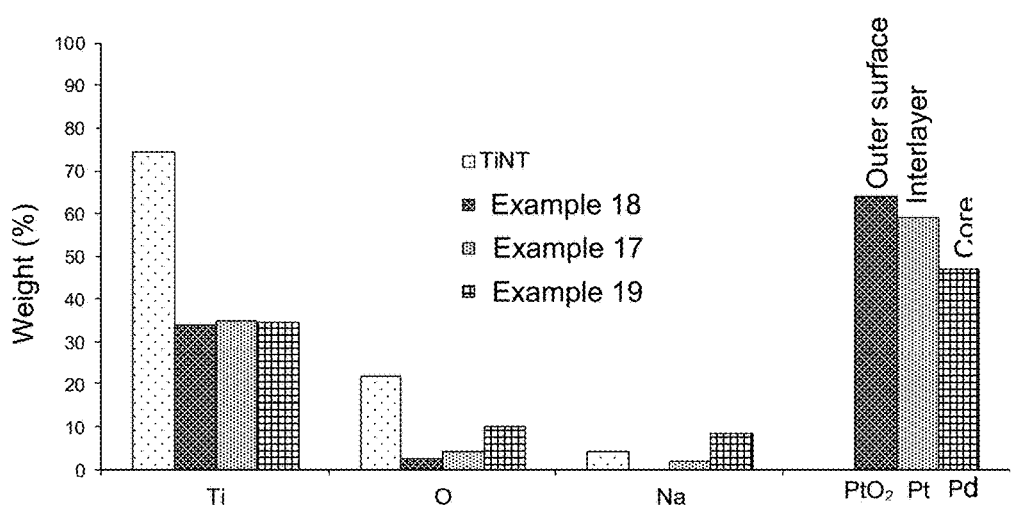
FIG. 21 is a graphical depiction of EDX quantitative analysis.

FIG. 20 is a sequenced series of Pt/TiNT with different morphologies, with a schematic representation of the core and interlayer. Platinum elements are doped on the outer surfaces, interlayer and on the core of the nanotubes by using tetraamine platinum (II) nitrate ($Pt(NH_3)_4.(NO_3)_2$) as precursor. From Table 6, doped samples present decreased BET surface area compared to titanate nanotubes. FIG. 21 is a graphical depiction of EDX quantitative analysis, of Pt/TiNT and Pd/TiNT. This analysis demonstrates the existence of palladium elements.

FIG. 20E-20F are TEM images of Pd/TiNT prepared from Palladium (II) chloride monohydrate ($Pd(NH_3)_4.Cl_2.H_2O$) as precursor. Palladium elements doped in the core of the titanate nanotubes. From Table 6, doped samples present decreased BET surface area compared to titanate nanotubes.

TABLE 6

| Name of the catalyst | $S_{BET}$ (m$^2$/g) | $V_{Total}$ (cm$^3$/g) |
| --- | --- | --- |
| TiNT | 293 | 1.19 |
| Platinum doped TiNT | 161 | 0.82 |
| Platinum Oxide TiNT | 205 | 0.90 |
| Palladium doped TiNT | 109 | 0.57 |

Figure 22A:
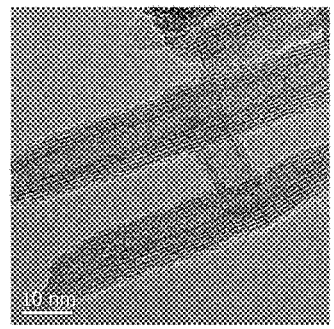
FIGS. 22A-22F are TEMS images showing vanadate element doped in the core and interlayer of the titanate nanotube, with FIG. 22G schematically representing the core and interlayer.
Figure 22B:
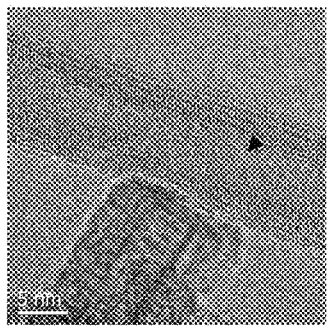
Figure 22C:
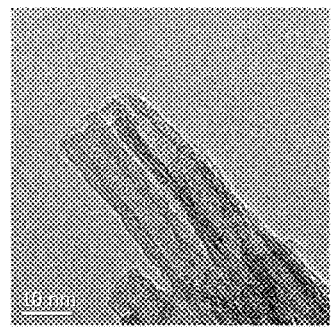
Figure 22D:
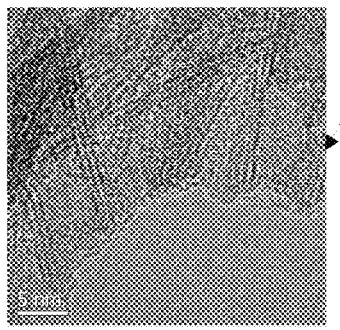
Figure 22E:
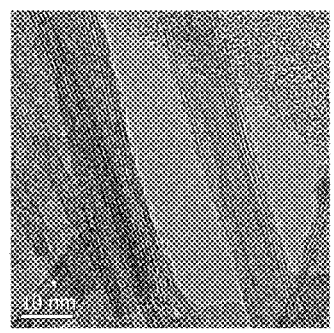
Figure 22F:
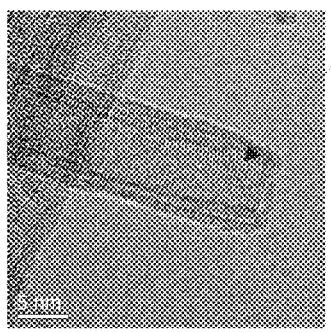
Figure 22G:
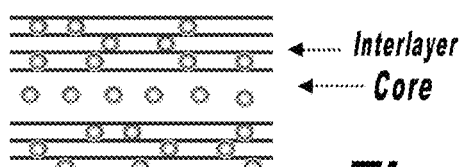
Figure 23:
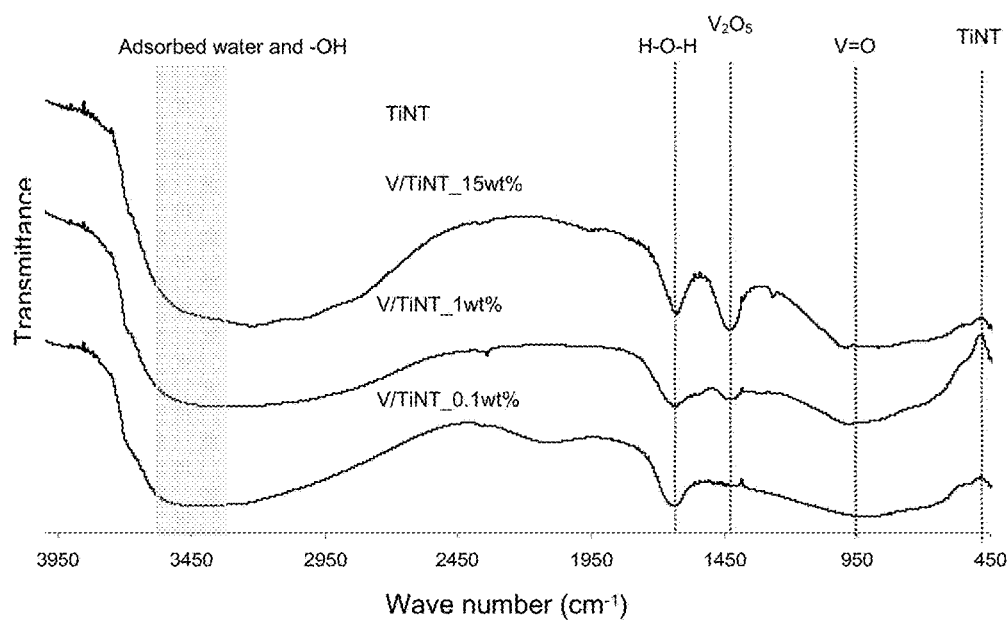
FIG. 23 is a sequenced series of graphical depictions showing FTIR spectra are the difference of $V_2O_5$ loading.
Figure 24:
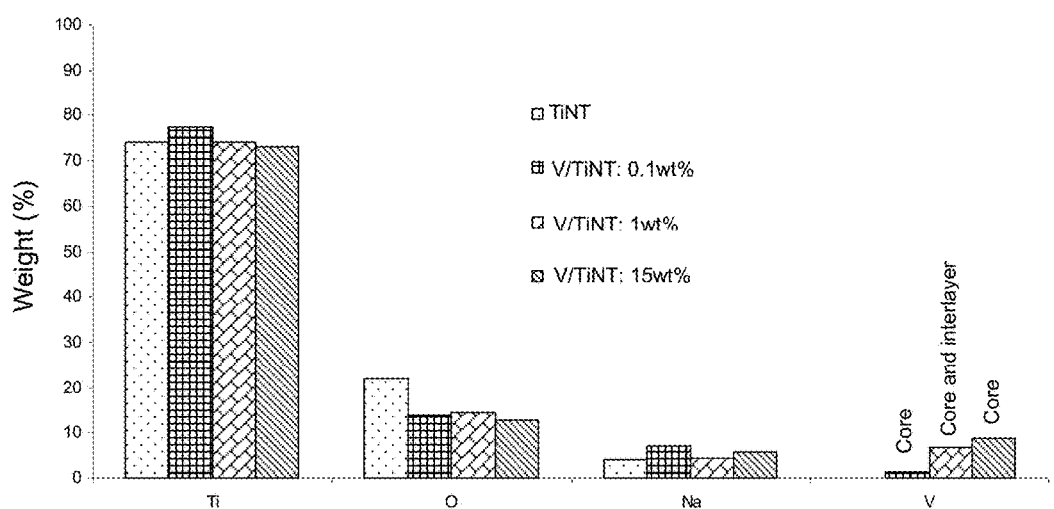
FIG. 24 is a graphical depiction showing EDX quantitative analysis of FIG. 23.
Figure 25:
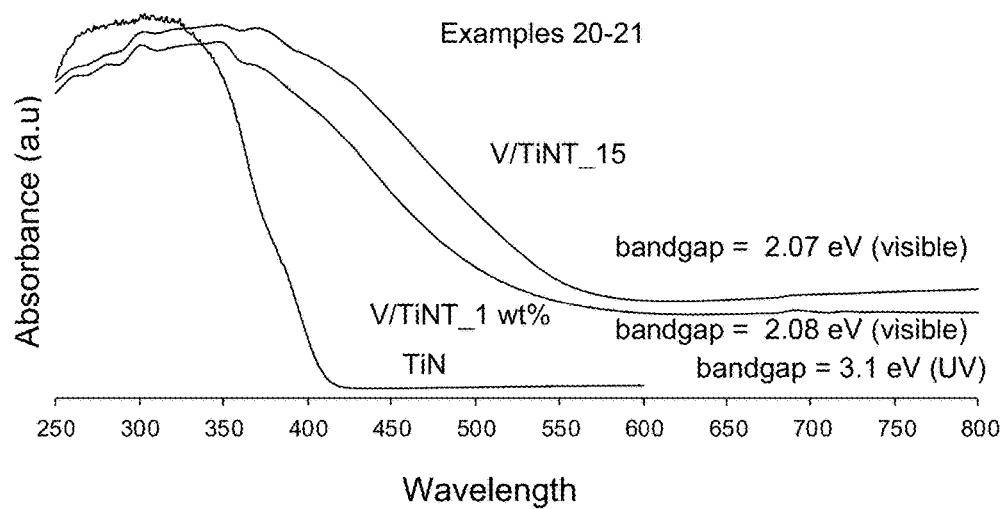
FIG. 25 is a graphical representation of UV-Vis spectra of V/TiNT with different loadings.

V/TiNT with different $V_2O_5$ loadings (15 wt %, 1 wt % and 0.1 wt %) are prepared by ammonium metavanadate ($NH_4VO_3$). FIGS. 22A-22F are TEMS images showing vanadate element doped in the core and interlayer of the titanate nanotube, with FIG. 22G schematically representing the core and interlayer. From Table 7, doped samples present decreased BET surface area compared to titanate nanotubes. FIG. 23 is a sequenced series of graphical depictions showing FTIR spectra are the difference of $V_2O_5$ loading. FIG. 24 is a graphical depiction showing EDX quantative analysis of FIG. 23, The existence of V element is verified by EDX quantitative analysis of FIG. 24. FIG. 25 is a graphical representation of UV-Vis spectra of V/TiNT with different $V_2O_5$ loadings. Band gaps of V/TiNT decreased from 3.1 to 2.07 eV.

TABLE 7

| Name of the catalyst | $S_{BET}$ (m$^2$/g) | $V_{Total}$ (cm$^3$/g) |
| --- | --- | --- |
| TiNT | 293 | 1.19 |
| V/TiNT_15 wt % | 232 | 0.70 |
| V/TiNT_1 wt % | 287 | 1.01 |
| V/TiNT_0.1 wt % | 237 | 0.98 |

FIG. 26 is a sequence of TEM images that show that Cu/TiNT prepared from Tetraamine copper(II) nitrate (TACN), [$Cu(NH_3)_4$]($NO_3)_2$]) by different mixture methods have different morphologies. By mixing tetraamine Cu (II) nitrate and titanate nanosheets with and without stirring Cu elements were doped in the core and both in the core and outer surfaces of the titanate nanotubes and corresponding EDX analysis verifies existence of Cu elements.

Figure 27A:
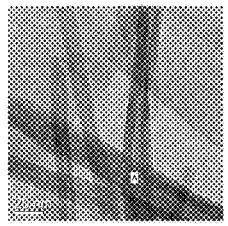
FIGS. 27A-D are TEM images of atomic scale doped Co/TiNT, depicted in FIGS. 27A and 27B and Zn/TiNT depicted in FIGS. 27C and 27D.
Figure 27B:
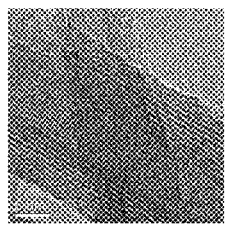
Figure 27C:
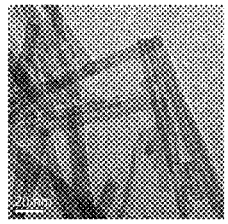
Figure 27D:
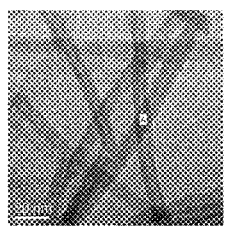
Figure 27E:
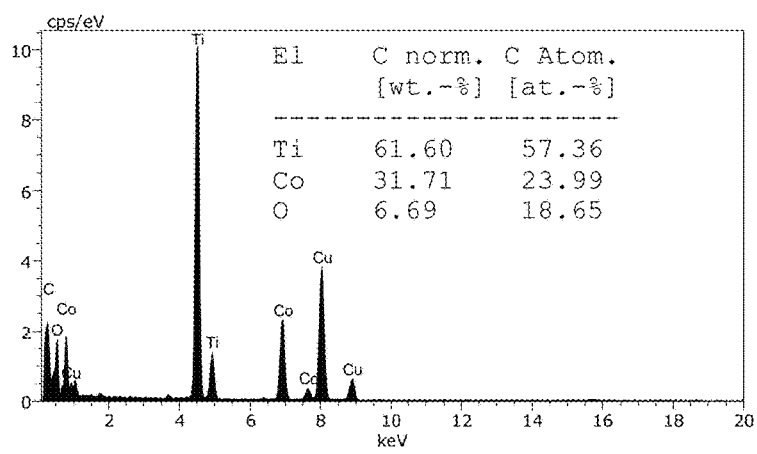
FIG. 27E is a spectral analysis for atomic scale doped Co/TiNT.
Figure 27F:
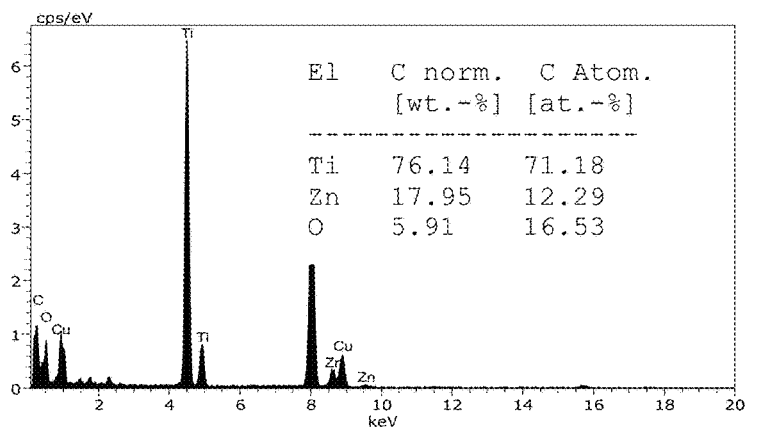
FIG. 27F is a spectral analysis for Zn/TiNT.

FIGS. 27A-D are TEM images of atomic scale doped Co/TiNT, depicted in FIGS. 27A and 27B and Zn/TiNT depicted in FIGS. 27C and 27D. FIG. 27E is a spectral analysis for atomic scale doped Co/TiNT. FIG. 27F is a spectral analysis for Zn/TiNT. For Co/TiNT and Zn/TiNT prepared from Cobalt (II) nitrate hexahydrate ($CoN_2O_6.6H_2O$) and Zinc sulphate.7 hydrate ($ZnSO_4.7H_2O$) respectively. Through EDX results shows the existence of Co and Zn elements. No Co or Zn nanoparticles observed from TEM images in FIG. 27 which indicates Co and Zn elements exists in atomic scale.

FIGS. 28A-28C are TEM images showing different dye compound doped nanotubes, with FIG. 28D showing the nanotube arrangement of FIGS. 28A-28C. FIG. 28A depicts the results using methyl orange/TiNT doped nanotubes. FIG. 28B depicts the results using Acid Blue 25/TiNT doped nanotubes. FIG. 28C depicts the results using Acid Yellow 34/TiNT doped nanotubes. FIG. 28D is a schematic representation of the arrangement of the nanotubes shown in FIGS. 28A-28C. Organic compounds doped titanate nanotubes Methyl Orange/TiNT, Acid Blue/TiNT and Acid Yellow/TiNT are prepared from different dye compounds, which are: methyl orange (MO) ($C_{14}H_{14}N_3NaO_3S$), acid blue (AB-25) ($C_{20}H_{13}N_2NaO_5S$) and acid yellow (AY-34) ($C_{16}H_{12}ClN_4NaO_4S$) respectively. Dye was doped on the core of the nanotubes.

FIG. 29 is a graphical representation of UV-V spectra resulting from band gap energy of the dye doped nanotubes of FIGS. 28A-28C. Band gap energy of dye doped nanotubes, calculated from UV-V spectra in FIG. 29, decreased from 3.1 to 2.75 eV.

EXAMPLES

Example-1.1 (Titanate Nanotube Prepared from Commercial Pure Anatase TiO$_2$, MW: 180° C. 90 Minutes)

0.05 g anatase TiO$_2$ was mixed with 8.55 g 10 M NaOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-1.2 (Titanate Nanotube Prepared from Commercial P25, MW: 180° C. 90 Minutes)

0.05 g $TiO_2$ was mixed with 8.55 g 10 M NaOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-1.3 (Titanate Nanotube Prepared from Hombikat UV 100 ($TiO_2$), MW: 180° C. 90 Minutes)

0.05 g $TiO_2$ was mixed with 8.55 g 10 M NaOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-1.4 (Titanate Nanotube Prepared from Modified $TiO_2$ Sol., MW: 180° C. 90 Minutes)

0.05 g $TiO_2$ sol. was mixed with 8.55 g 10 M NaOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-1.5 (Titanate Nanotube Prepared from Titanium Carbide (TiC), MW: 180° C. 90 Minutes)

Firstly, 0.05 g Titanium carbide (TiC) is annealing at 350° C. for 2 hours. After annealing, this sample was mixed with 8.55 g 10 M NaOH suspension followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-1.6 (Titanate Nanofiber Prepared from Titanium Carbide (TiC), MW: 180° C. 90 Minutes)

0.05 g Titanium carbide (TiC) was mixed with 8.55 g 10 M NaOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanofiber.

Example-1.7 (Titanate Nanotube Prepared from Titanium Nitride (TiN), MW: 180° C. 90 Minutes)

0.05 g Titanium nitride (TiN) was mixed with 8.55 g 10 M NaOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanocomposite (0D nanoparticles and 1D nanotubes).

Example-2.1 (Titanate Nanotube Prepared from Commercial Pure Anatase $TiO_2$, MW: 180° C. 30 Minutes)

A homogeneous mixture of Example 1.1 is prepared. Then, the suspension was treated under microwave irradiation at 180° C. for 30 minutes to obtain nanosheet. The sample was then centrifuged and washed with 0.1M HCl until pH value of the washing solution reaches 6~7 followed by drying at 65° C. overnight to obtain nanotube Example-2.2 (Titanate Nanotube Prepared from Commercial Pure Anatase $TiO_2$, MW: 180° C. 360 Minutes)

A homogeneous mixture of Example 1.1 is prepared. Then, the suspension was treated under microwave irradiation at 180° C. for 360 minutes to obtain nanosheet. The sample was then centrifuged and washed with 0.1M HCl until pH value of the washing solution reaches 6~7 followed by drying at 65° C. overnight to obtain nanotubes.

Example-3 (Titanate Nanotube Prepared from Commercial Pure Anatase $TiO_2$, MW: 195° C. 90 Minutes)

A homogeneous mixture of Example 1.1 is prepared. Then, the suspension was treated under microwave irradiation at 195° C. for 90 minutes to obtain nanosheet. The sample was then centrifuged and washed with 0.1M HCl until pH value of the washing solution reaches 6~7 followed by drying at 65° C. overnight to obtain nanotubes.

Example-4 (Titanate Nanotube Prepared from Commercial Pure Anatase $TiO_2$, MW: 180° C. 30 Minutes, Washing with DDI (Room Temperature))

MW treated intermediate stage of Example 1.1 is prepared. This sample was then centrifuged and washed with double de-ionized (DDI) water at room temperature until pH value of the washing solution reaches 6~7 followed by drying at 65° C. overnight to obtain nanotubes.

Example-5 (Titanate Nanotube Prepared from Commercial Pure Anatase $TiO_2$, MW: 180° C. 30 Minutes, Hot Water as a Washing Solution (80° C.))

MW treated intermediate stage of Example 1.1 is prepared. This sample was then centrifuged and washed with double de-ionized (DDI) water at 80° C. until pH value of the washing solution reaches 6~7 followed by drying at 65° C. overnight to obtain nanotubes.

Example-6 (Titanate Nanotube Prepared from Commercial Pure Anatase $TiO_2$, MW: 180° C. 30 Minutes, Ethanol as a Washing Solution (Absolute≥99.9%))

MW treated Nanosheets of Example 1.1 is prepared. This sample was then centrifuged and washed with ethanol (absolute≥99.9%) until pH value of the washing solution reaches 6~7 followed by drying at 65° C. overnight to obtain nanotubes.

Example-7 (Titanate Nanotube Prepared from Commercial Pure Anatase $TiO_2$, MW: 200° C. 120 Minutes, Ethylene Glycol as an Organic Solvent)

0.05 g anatase $TiO_2$ was mixed with 8.55 g ethylene glycol (EG) followed by stirring at least two or three hours for homogeneous mixture. Then, the suspension was treated under microwave irradiation at 200° C. for 120 minutes to obtain nanosheet. The sample was then centrifuged and washed with ethanol (absolute≥99.9%) until pH value of the washing solution reaches 6~7 followed by drying at 65° C. overnight to obtain nanotubes.

Example-8 (Titanate Nanotube Prepared from Commercial Pure Anatase $TiO_2$, MW Treatment: 300° C. 120 Minutes, Glycerol as an Organic Solvent)

0.05 g anatase $TiO_2$ was mixed with 8.55 g glycerol solution followed by stirring at least two or three hours for homogeneous mixture. Then, the suspension was treated under microwave irradiation at 300° C. for 120 minutes to obtain nanosheet. The sample was then centrifuged and washed with ethanol (absolute≥99.9%) until pH value of the washing solution reaches 6~7 followed by drying at 65° C. overnight to obtain nanotubes.

Example-9 (Titanate Nanotube Prepared from Commercial P25, MW: 180° C. 30 Minutes, Used KOH as Solvent)

0.05 g $TiO_2$ was mixed with 8.55 g 10 M KOH solution followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-10 (Titanate Nanotube Prepared from Commercial P25, MW: 180° C. 90 Minutes, Used (1:1) TMAOH & NaOH as Solvent)

0.05 g $TiO_2$ was mixed with 8.55 g [TMAOH & NaOH (1:1) molar ratio] suspension followed by stirring at least two or three hours for homogeneous mixture. Then, the suspension was treated under microwave irradiation at 180° C. for 90 minutes to obtain nanosheet. The sample was then centrifuged and washed with 0.1M HCl until pH value of the washing solution reaches 6~7 followed by drying at 65° C. overnight to obtain nanotubes.

Example-11 (Au Doped Titanate Nanotube Prepared from Commercial Pure Anatase $TiO_2$, MW: 180° C. 90 Minutes)

MW treated nanosheets of Example 1.1 is prepared. The sample was then centrifuged and washed with 1 mM $[AuCl_4]^-$ aqueous solution (hydrogen tetrachloroaurate (III) trihydrate, $HAuCl_4.3H_2O$) until pH value of the washing solution reaches 6~7 followed by drying at 65° C. overnight to get Au doped nanotubes.

Example-12 (Au Doped Titanate Nanotube Prepared from Commercial Pure Anatase $TiO_2$, MW: 180° C. 30 Minutes)

Firstly, cationic gold (III) complexes, (Tetraammine gold (III) nitrate, $[Au(NH_3)_4](NO_3)_3]$) was prepared from hydrogen tetrachloroaurate (III) trihydrate, $[HAuCl_4.3H_2O]$ in presence of excess aqueous ammonia.

MW treated nanosheets of Example 1.1 is prepared. The sample was then centrifuged and washed with 10 mM of as prepared cationic gold (III) complexes $[Au(NH_3)_4]^{3+}$ solution until pH value of the washing solution reaches 6~7 followed by drying at 65° C. overnight to get cationic Au (III) complexes, $[Au(NH_3)_4]^{3+}$ doped nanotubes.

Example-13 (Au Oxide Doped Titanate Nanotube Prepared from Commercial Pure Anatase $TiO_2$, MW: 180° C. 30 Minutes)

MW treated nanosheets of Example 1.1 is prepared and sample was then centrifuged. Diluted as prepared $[AuCl_4]^-$ aqueous solution (hydrogen tetrachloroaurate (III) trihydrate, $HAuCl_4.3H_2O$) two times and nanosheets disperse in this solution and washed until pH value of the washing solution reaches 6~7 followed by drying at 65° C. overnight to get Au doped nanotube Then, the sample was calcined at 300° C. for 3 hours in tubular furnace with oxygen flow rate of 10 $cm^3$/min to prepare gold oxide doped nanotubes.

Example-14 (Ag Doped Titanate Nanotube Prepared from Commercial Pure Anatase $TiO_2$, MW: 180° C. 30 Minutes)—Ag/TiNT: Higher $Ag^+$ Loading n Ex Situ Process)

MW treated Nanosheet of Example 1.1 is prepared. The sample was then centrifuged and washed with 100 mM $Ag^+$ aqueous acid solution ($AgNO_3$) until pH value of the washing solution reaches 6~7 followed by drying at 65° C. overnight to obtain Ag doped nanotubes. The resulting characteristics are shown in FIG. 14.

Example-15 ((Ag Doped Titanate Nanotube Prepared from Commercial Pure Anatase $TiO_2$, MW: 180° C. 30 Minutes)—Ag/TiNT: Higher $Ag^+$ Loading In Situ Process)

A homogeneous mixture of Example 1.1 is prepared. Then, 1 wt % of silver nitrate, $AgNO_3$ (Ti:Ag=1:1) was mixed in this solution and again stirring in dark environment for several hours to prepare metal/titania mixed precursor. The suspension was treated under microwave irradiation at 180° C. for 30 minutes to prepare metal doped nanosheet. The sample was then centrifuged and washed with 0.1M HCl until pH value of the washing solution reaches 6~7 followed by drying at 65° C. overnight to obtain Ag doped nanotubes. The resulting characteristics are shown in FIG. 14.

Example-16 ((Ag Doped Titanate Nanotube Prepared from Commercial Pure Anatase $TiO_2$, MW: 180° C. 30 Minutes)—Ag/TiNT: Lower $Ag^+$ Loading In Situ Process)

A homogeneous mixture of Example 1.1 is prepared. Then, 0.1 wt % of silver nitrate, $AgNO_3$ (Ti:Ag=1:1) was mixed in this solution and again stirring in dark environment for several hours to prepare metal/titania mixed precursor. The suspension was treated under microwave irradiation at 180° C. for 30 minutes to prepare metal doped nanosheet. The sample was then centrifuged and washed with 0.1M HCl until pH value of the washing solution reaches 6~7 followed by drying at 65° C. overnight to obtain Ag doped nanotubes. The resulting characteristics are shown in FIG. 14.

Example-17 (Pt Doped Titanate Nanotube Prepared from Commercial Pure Anatase $TiO_2$, MW: 180° C. 30 Minutes)

MW treated Nanosheet of Example 1.1 is prepared. The sample was then centrifuged and washed with 10 mM platinum aqueous solution (Tetraammine Platinum (II) nitrate $(Pt(NH_3)_4.(NO_3)_2)$ until pH value of the washing solution reaches 6~7 followed by drying at 65° C. overnight to obtain Pt (II) doped nanotubes. The resulting characteristics are shown in FIG. 21.

Example-18 (Pt Oxide Doped Titanate Nanotube Prepared from Commercial Pure Anatase $TiO_2$, MW: 180° C. 30 Minutes)

MW treated nanosheets of Example 1.1 is prepared and sample was then centrifuged. Diluted as prepared platinum aqueous solution (Tetraammine Platinum (II) nitrate $(Pt(NH_3)_4.(NO_3)_2)$ two times and nanosheets disperse in this solution and washed until pH value of the washing solution reaches 6~7 followed by drying at 65° C. overnight to get Pt (II) doped nanotubes. Then the sample was calcined at 300° C. for 3 hours in tubular furnace with oxygen flow rate of 10 $cm^3$/min to prepare platinum oxide doped nanotubes. The resulting characteristics are shown in FIG. 21.

Example-19 (Pd Doped Titanate Nanotube Prepared from Commercial Pure Anatase $TiO_2$, MW: 180° C. 30 Minutes)

MW treated Nanosheet of Example 1.1 is prepared. The sample was then centrifuged and washed with 100 mM palladium aqueous solution (Palladium (II) chloride monohydrate $(Pd(NH_3)_4.Cl_2.H_2O)$ until pH value of the washing solution reaches 6~7 followed by drying at 65° C. overnight to obtain Pd (II) doped nanotubes. The resulting characteristics are shown in FIG. 21.

Example-20 ((V Doped Titanate Nanotube Prepared from as Prepared Titanate Nanotube, MW: 180° C. 90 Minutes)—$V_2O$: 15 Wt %)

Titanate nanotube of Example 1.1 is prepared. This sample is then dispersed in 42 mM ammonium metavanadate $(NH_4VO_3)$ aqueous solution to obtain $V_2O_5$ loading of 15 wt %. The sample was dried at 60° C. by using rotary evaporator to prepare V doped nanotubes. The resulting characteristics are shown in FIG. 25.

Example-21 ((V Doped Titanate Nanotube Prepared from as Prepared Titanate Nanotube, MW: 180° C. 90 Minutes)—$V_2O_5$: 1 Wt %)

Titanate nanotube of Example 1.1 is prepared. This sample is then dispersed in 42 mM ammonium metavanadate $(NH_4VO_3)$ aqueous solution to obtain $V_2O_5$ loading of 1 wt %. The sample was dried at 60° C. by using rotary evaporator to prepare V doped nanotubes. The resulting characteristics are shown in FIG. 25.

Example-22 ((V Doped Titanate Nanotube Prepared from as Prepared Titanate Nanotube, MW: 180° C. 90 Minutes)—$V_2O_5$: 0.1 Wt %)

Titanate nanotube of Example 1.1 is prepared. This sample is then dispersed in 42 mM ammonium metavanadate $(NH_4VO_3)$ aqueous solution to obtain $V_2O_5$ loading of 0.1 wt %. The sample was dried at 60° C. by using rotary evaporator to prepare V doped nanotubes.

Example-23 ((Cu Doped Titanate Nanotube Prepared from Commercial Pure Anatase $TiO_2$, MW: 180° C. 90 Minutes)—Cationic Cu Complexes Doped TiNT, 24 Hours Stirred)

Firstly, cationic Cu(II) complexes, (Tetraammine copper (II) nitrate (TACN), $[Cu(NH_3)_4](NO_3)_2]$) called fulminating copper, was prepared from copper(II) nitrate trihydrate $[Cu(NO_3)_2.3H_2O]$ in presence of excess aqueous ammonia.

MW treated nanosheets of Example 1.1 is prepared. The sample was then centrifuged and washed with 10 mM of as prepared cationic Cu (II) complexes $[Cu(NH_3)_4]^{+2}$ solution followed by stirring for 24 hours. Repeat the washing with Cu (II) complexes $[Cu(NH_3)_4]^{+2}$ solution until pH value of the washing solution reaches 6~7 followed by drying at 65° C. overnight to get cationic Cu (II) complexes, $[Cu(NH_3)_4]^{2+}$ doped nanotubes.

Example-24 ((Cu Doped Titanate Nanotube Prepared from Commercial Pure Anatase $TiO_2$, MW: 180° C. 90 Minutes)—Cationic Cu Complexes Doped TiNT, 24 Hours Stirred)

MW treated nanosheets of Example 1.1 is prepared. The sample was then centrifuged and washed with 10 mM of as prepared cationic Cu (II) complexes $[Cu(NH_3)_4]^{+2}$ solution. Keep this sample in dark place for 24 hours without stirring. Repeat the washing with Cu (II) complexes $[Cu(NH_3)_4]^{+2}$ solution until pH value of the washing solution reaches 6~7 followed by drying at 65° C. overnight to get cationic Cu (II) complexes, $[Cu(NH_3)_4]^{2+}$ doped nanotubes.

Example-25 ((Co Doped Titanate Nanotube Prepared from Commercial Pure Anatase $TiO_2$, MW: 180° C. 30 Minutes)—Co/TiNT: Atomic Scale Doping)

MW treated nanosheet of Example 1.1 is prepared. The sample was then centrifuged and washed with 100 mM $Co^{2+}$ aqueous solution (Cobalt (II) nitrate hexahydrate ($CoN_2O_6 \cdot 6H_2O$)) until pH value of the washing solution reaches 6~7 followed by drying at 65° C. overnight to get Co doped nanotubes.

Example-26 ((Zn Doped Titanate Nanotube Prepared from Commercial Pure Anatase $TiO_2$, MW: 180° C. 30 Minutes)—Zn/TiNT: Atomic Scale Doping)

MW treated nanosheet of Example 1.1 is prepared. The sample was then centrifuged and washed with 100 mM $Zn^{2+}$ aqueous solution (Zinc sulphate.7 hydrate ($ZnSO_4 \cdot 7H_2O$)) until pH value of the washing solution reaches 6~7 followed by drying at 65° C. overnight to get Zn doped nanotubes.

Example-27 (Methyl Orange (MO) Doped Titanate Nanotube Prepared from Commercial Pure Anatase $TiO_2$, MW: 180° C. 30 Minutes)

MW treated nanosheet of Example 1.1 is prepared. The sample was then centrifuged and washed with 1 mM MO aqueous solution ($C_{14}H_{14}N_3NaO_3S$) at 80° C. until pH value of the washing solution reaches 6~7 followed by drying at 65° C. overnight to get MO doped nanotubes.

Example-28 (Acid Blue 25 (AB-25) Doped Titanate Nanotube Prepared from Commercial Pure Anatase $TiO_2$, MW: 180° C. 30 Minutes)

MW treated nanosheet of Example 1.1 is prepared. The sample was then centrifuged and washed with 1 mM AB-25 aqueous solution ($C_{20}H_{13}N_2NaO_5S$) at 80° C. until pH value of the washing solution reaches 6~7 followed by drying at 65° C. overnight to get AB-25 doped nanotubes.

Example-29 (Acid Yellow 34 (AY-34) Titanate Nanotube Prepared from Commercial Pure Anatase $TiO_2$, MW: 180° C. 30 Minutes)

MW treated nanosheet of Example 1.1 is prepared. The sample was then centrifuged and washed with 1 mM AY-34 aqueous solution ($C_{16}H_{12}ClN_4NaO_4S$) at 80° C. until pH value of the washing solution reaches 6~7 followed by drying at 65° C. overnight to get AY-34 doped nanotubes.

CONCLUSION

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. A multi-walled titanium-based nanotube array containing one or more metal or non-metal dopants wherein said dopants comprise ions, compounds, clusters and particles located on at least one of a surface, inter-wall space and core of the nanotube, wherein the nanotube array comprises:
 a nanotube structure having at least one dopant located on the surface and a second dopant located in the inter-wall space of the nanotube, or one dopant located on the surface and a second dopant located in the core of the nanotube, or one dopant located on the core and a second dopant located on the inter-wall space of the nanotube, wherein the dopants comprise one or more dopants selected from the group of:
 inorganic dopant materials selected from the group consisting of Group IB, IIB, IVB, V and VIII elements,
 materials selected from the group consisting of V, Co, Cu, Zn, Pd, Ag, Pt and Au, used as metal or nonmetal dopants, and
 a non metallic organic compound comprising a non metallic dye.

2. The multi-walled titanium-based nanotube array as described in claim 1, further comprising:
 at least first and second dopants, in the form of metal or non-metal ions, compounds, clusters or particles, wherein the first and second dopants have a configuration selected from the group consisting of:
 the first dopant located on the surface and the second dopant located in the inter-wall space of the nanotube;
 the first dopant located on the surface and the second dopant located in the core of the nanotube; and
 the first dopant located on the core and the second dopant located on the inter-wall space of the nanotube; and
 a third dopant in the form of metal or non-metal ions, compounds, clusters or particles, wherein the first, second and third dopants have a configuration of the first dopant located on the surface, the second dopant located in the inter-wall space and the third dopant located in the core of the nanotube,
 wherein the dopants comprise:
 inorganic dopant materials selected from the group consisting of Group IB, JIB, IVB, V and VIII elements, or
 materials selected from the group consisting of V, Co, Cu, Zn, Pd, Ag, Pt and Au, used as metal or nonmetal dopants, or
 a non-metallic organic compound,
 wherein the dopants comprise a non-metallic dye.

3. The multi-walled titanium-based nanotube array as described in claim 2 wherein said dye comprises at least one material selected from the group consisting of acid Blue, methyl orange, acid yellow, copper phthalocyanine-3,4',4'',4'''-tetrasulfonic acid tetrasodium salt and reactive Black 5.

4. A method of preparation of multi-walled titanium-based nanotubes containing a metal and/or non-metal dopants selectively located on at least one of a surface of the nanotube, as an interlayer within the nanotube, or a core of the nanotube, the method comprising:
 providing a titanium precursor;
 converting the titanium precursor into titanium-based layered materials to form titanium-based nanosheets; and
 transforming the titanium-based nanosheets to multi-walled titanium-based nanotubes, thereby providing a nanotube structure having at least one dopant located on the surface and a second dopant located in the inter-wall space (interlayer) of the nanotube, or one dopant located on the surface and a second dopant located in the core of the nanotube, or one dopant located on the core and a second dopant located on the inter-wall space of the nanotube.

5. The method as described in claim 4, further comprising:
 in an ex situ process, forming titanium nanostructure from the titanium precursor by using microwave (MW) assisted alkaline hydrothermal synthesis by preparing a homogeneous mixture of titanium followed by microwave hydrothermal irradiation to produce titanate nanosheets in an intermediate stage;

mixing a transition metal in an aqueous acid solution or water, resulting in a transformation mechanism; and doping the formed titanium nanostructures using a microwave hydrothermal irradiation process.

6. The method as described in claim 4, further comprising:

converting the titanium precursor into titanium-based nanosheets by hydrothermal or solvothermal treatment in a solution containing an inorganic of 2 M to 15 M or organic base of 2 M to 5 M, wherein said inorganic and organic base comprises a material selected from the group consisting of sodium hydroxide (NaOH), potassium hydroxide (KOH), tetramethylammonium hydroxide (TMAOH), tetraethylammonium hydroxide (TEAOH), and tetrapropylammonium hydroxide (TPAOH); and applying continuous or pulsating microwave irradiation during said converting.

7. The method as described in claim 6, further comprising providing the titanium precursor for the dopant for rinsing at a concentration of the titanium precursor of 10 mM to 100 mM.

8. The method as described in claim 4, further comprising:

transforming the titanium-based nanosheets into multi-walled titanium based nanotubes by the use of a precursor solution having an anionic or cationic charge, the transforming comprising:

for transforming negatively-charged titanium-based nanosheets into multi-walled titanium-based nanotubes containing metal and/or non-metal dopants by single, sequential or combination of the following steps:
 a. rinsing the titanium-based nanosheets in a solution of a concentrated anionic precursor for the dopant to obtain multi-walled titanium-based nanotubes with dopants on the surface;
 b. rinsing the titanium-based nanosheets in a solution of a cationic precursor for the dopant to obtain multi-walled titanium-based nanotubes with dopants in the inter-wall spaces;
 c. rinsing the titanium-based nanosheets in a solution of the dilute anionic precursor for the dopant to obtain multi-walled titanium-based nanotubes with dopants in the core, or
 a. rinsing with water or acid solution to obtain multi-walled titanium-based nanotubes containing metal and/or nonmetal dopants;
 b. rinsing with a concentrated anionic solution of a precursor for a dopant to introduce additional dopant on surface;
 c. rinsing with a cationic solution of a precursor for a dopant to introduce additional dopant in the inter-wall space;
 d. rinsing with a dilute anionic solution of a precursor for a dopant to introduce additional dopant in the core; and for transforming positively-charged titanium-based nanosheets into multi-walled titanium-based nanotubes containing a metal and/or non-metal dopants by single, sequential or combination of the following steps:
 a. rinsing the titanium-based nanosheets in a solution of the concentrated cationic precursor for the dopant to obtain multi-walled titanium-based nanotubes with dopants on the surface;
 b. rinsing the titanium-based nanosheets in a solution of the anionic precursor for the dopant to obtain multi-walled titanium-based nanotubes with dopants in the inter-wall spaces;
 c. rinsing the titanium-based nanosheets in a solution of the dilute cationic precursor for the dopant to obtain multi-walled titanium-based nanotubes with dopants in the core, or
 a. rinsing with water or acid solution to obtain multi-walled titanium-based nanotubes containing metal and/or nonmetal dopants;
 b. rinsing with a concentrated cationic solution of a precursor for a dopant to introduce additional dopant on surface;
 c. rinsing with a anionic solution of a precursor for a dopant to introduce additional dopant in the inter-wall space;
 d. rinsing with a dilute cationic solution of a precursor for a dopant to introduce additional dopant in the core.

9. The method as described in claim 4, wherein said titanium precursor comprises a material selected from the group consisting of titanium, titanium chloride, titanium alkoxides, titanium oxides in the form of solutions and powder, anatase, rutile and mixed phase, titanium nitride, titanium carbide and titanium-containing ceramics and composites.

10. The method as described in claim 4, further comprising selecting, as a dopant for the doping of the formed titanium nanostructures, a transition metal.

11. A method as described in claim 4, further comprising selecting, as a dopant for the doping of the formed titanium nanostructures, a material selected from the group consisting of Au, Ag, Pt, Pd, Co, Cu, V, Zn.

12. A method as described in claim 4, further comprising selecting, as a dopant for the doping of the formed titanium nanostructures, a material selected from the group consisting of $Au^{3+}$, $Ag^+$, $Pt^{2+}$, $Pd^{2+}$, $Co^{2+}$, $Cu^{2+}$, $V^{5+}$, $Zn^{2+}$.

13. The method as described in claim 4, further comprising heat treating multi-walled titanium-based nanotubes containing dopants in inter-wall space at 50° C. to 400° C.

14. The method as described in claim 4, further comprising applying hydrothermal treatment at temperatures of 180° C. to 200° C.

15. The method as described in claim 4, further comprising applying microwave hydrothermal irradiation from 180° C. to 200° C. for 30 to 360 minutes.

16. The method as described in claim 4, further comprising carrying out a solvothermal treatment in an alcohol compound, glycerol, propylene glycol and ethylene glycol at temperatures of 50 to 250° C.

17. The method as described in claim 4, further comprising rinsing the nanotubes with an acid, wherein said acid comprises a material selected from the group consisting of hydrochloric acid, nitric acid, sulphuric acid and acetic acid, in a concentration of 1 mM to 700 mM.

18. The method as described in claim 4, further comprising preparing doped 1D titanium-containing nanomaterial including nanofiber and nanorods by heat treatment of multi-walled titanium-based nanotubes containing metal or non-metal dopants at temperatures above 400° C.

19. The method as described in claim 4, further comprising:

extracting doped titanate nanotubes by using centrifugation; and drying the titanate nanotubes.

20. A doped titanium nanostructure formed in accordance with the process of claim 4.

21. The method as described in claim 4, wherein the dopants comprise:

inorganic dopant materials selected from the group consisting of Group IB, JIB, IVB, V and VIII elements, or materials selected from the group consisting of V, Co, Cu, Zn, Pd, Ag, Pt and Au, used as metal or nonmetal dopants, or a non-metallic organic compound.

22. A method of preparation of multi-walled titanium-based nanotubes comprising non-metal dopants located on a core of the nanotube, the method comprising:

providing a titanium precursor;

converting the titanium precursor into titanium-based layered materials to form titanium-based nanosheets; and transforming the titanium-based nanosheets to multi-walled titanium-based nanotubes, wherein the non-metal dopants comprise non-metal dyes.

23. The method as described in claim 22, wherein said dye comprises at least one material selected from the group consisting of acid Blue, methyl orange, acid yellow, copper phthalocyanine-3,4',4",4'"-tetrasulfonic acid tetrasodium salt and reactive Black 5.

* * * * *